US012584863B2

(12) United States Patent
Sanden et al.

(10) Patent No.: US 12,584,863 B2
(45) Date of Patent: Mar. 24, 2026

(54) LASER INDUCED BREAKDOWN SPECTROSCOPY FOR GEOLOGICAL ANALYSIS

(71) Applicant: ENERSOFT INC., Calgary (CA)

(72) Inventors: Grant I. Sanden, Calgary (CA);
Yannai Z.R. Segal, Calgary (CA);
Mikhail Kostousov, Calgary (CA)

(73) Assignee: ENERSOFT INC., Calgary (CA)

( * ) Notice: Subject to any disclaimer, the term of this patent is extended or adjusted under 35 U.S.C. 154(b) by 96 days.

(21) Appl. No.: 18/393,159

(22) Filed: Dec. 21, 2023

(65) Prior Publication Data

US 2024/0167961 A1 May 23, 2024

Related U.S. Application Data

(63) Continuation of application No. PCT/CA2022/051025, filed on Jun. 25, 2022.
(Continued)

(51) Int. Cl.
*G01N 21/71* (2006.01)
*G01N 33/24* (2006.01)

(52) U.S. Cl.
CPC .......... *G01N 21/718* (2013.01); *G01N 33/24* (2013.01); *G01N 2201/06113* (2013.01);
(Continued)

(58) Field of Classification Search
CPC ................. G01N 21/718; G01N 33/24; G01N 2201/06113; G01N 2201/0636; G01N 2201/08; G01N 2201/103
See application file for complete search history.

(56) References Cited

U.S. PATENT DOCUMENTS

| | | | |
|---|---|---|---|
| 3,889,113 A | 6/1975 | Rhodes | |
| 4,560,275 A | 12/1985 | Goetz | |

(Continued)

FOREIGN PATENT DOCUMENTS

| | | | |
|---|---|---|---|
| CA | 2720667 A1 | 10/2009 | |
| CA | 2750255 A1 | 7/2010 | |

(Continued)

OTHER PUBLICATIONS

Barton et al. "Discrimination of Natural Fractures From Drilling-Induced Wellbore Failures in Wellbore Image Data—Implications for Reservoir Permeability". SPE Res Eval & Eng 5 (03): 249-254. Jun. 1, 2002 Paper No. SPE-78599-PA. https://doi.org/10.2118/78599-PA, Jun. 1, 2002, 6 pages.
(Continued)

*Primary Examiner* — Jamil Ahmed
(74) *Attorney, Agent, or Firm* — Smith Baluch LLP

(57) ABSTRACT

Laser induced breakdown spectroscopy (LIBS) devices for analysis of geological and related samples, and related methods. In the method, a scanning table having a geological core is moved from a start position to an end position for each position in a plurality of positions of the scanning table corresponding to an e region of interest of the geological core. At each position, laser ablation is performed on the exposed surface of the geological core using an oscillating planar focus laser. Contemporaneously with performing laser ablation on the exposed surface of the geological core, spectroscopy is permitted on the emitted light received by a fiber optic receiver sharing an optical path with the oscillating planar focus laser.

32 Claims, 12 Drawing Sheets

Related U.S. Application Data

(60) Provisional application No. 63/215,005, filed on Jun. 25, 2021.

(52) U.S. Cl.
CPC ............... *G01N 2201/0636* (2013.01); *G01N 2201/08* (2013.01); *G01N 2201/103* (2013.01)

(56) References Cited

U.S. PATENT DOCUMENTS

| | | |
|---|---|---|
| 4,852,135 A | 7/1989 | Anisovich et al. |
| 5,107,527 A | 4/1992 | Sipila et al. |
| 5,187,727 A | 2/1993 | Vogler et al. |
| 5,325,416 A | 6/1994 | Saito et al. |
| 5,657,363 A | 8/1997 | Hossain et al. |
| 5,712,891 A | 1/1998 | Benony et al. |
| 5,721,759 A | 2/1998 | Raatikainen |
| 5,742,658 A | 4/1998 | Tiffin et al. |
| 5,832,054 A | 11/1998 | Kuwabara |
| 5,883,583 A | 3/1999 | Kishino |
| 5,937,026 A | 8/1999 | Satoh |
| 6,052,429 A | 4/2000 | Ohno et al. |
| 6,108,398 A | 8/2000 | Mazor et al. |
| 6,108,399 A | 8/2000 | Hernandez-Guerra et al. |
| 6,233,307 B1 | 5/2001 | Golenhofen |
| 6,266,390 B1 | 7/2001 | Sommer, Jr. et al. |
| 6,292,532 B1 | 9/2001 | Kawahara et al. |
| 6,295,333 B1 | 9/2001 | Tamura |
| 6,314,158 B1 | 11/2001 | Shiota et al. |
| 6,345,086 B1 | 2/2002 | Ferrandino et al. |
| 6,370,220 B1 | 4/2002 | Stoop |
| 6,381,303 B1 | 4/2002 | Vu et al. |
| 6,400,795 B2 | 6/2002 | Yagi |
| 6,421,415 B1 | 7/2002 | Peczkis et al. |
| 6,426,993 B1 | 7/2002 | Satoh |
| 6,453,002 B1 | 9/2002 | Mazor et al. |
| 6,477,227 B1 | 11/2002 | Kaiser et al. |
| 6,512,810 B1 | 1/2003 | Haszler et al. |
| 6,522,718 B2 | 2/2003 | Sato |
| 6,577,705 B1 | 6/2003 | Chang et al. |
| 6,677,162 B1 | 1/2004 | Wendelbo et al. |
| 6,697,454 B1 | 2/2004 | Nicolich et al. |
| 6,754,304 B1 | 6/2004 | Kumakhov |
| 6,801,595 B2 | 10/2004 | Grodzins et al. |
| 6,806,093 B2 | 10/2004 | Wendelbo et al. |
| 6,810,106 B2 | 10/2004 | Sato |
| 6,823,041 B2 | 11/2004 | Greenbank et al. |
| 6,826,253 B2 | 11/2004 | Greenbank et al. |
| 6,826,483 B1 | 11/2004 | Anderson et al. |
| 6,850,592 B2 | 2/2005 | Schramm et al. |
| 6,881,363 B2 | 4/2005 | Carlson et al. |
| 6,952,260 B2 | 10/2005 | Xiao |
| 6,980,283 B1 | 12/2005 | Aggarwal |
| 7,020,238 B1 | 3/2006 | Kantonen et al. |
| 7,065,174 B2 | 6/2006 | Sipila et al. |
| 7,229,064 B2 | 6/2007 | Miller et al. |
| 7,233,643 B2 | 6/2007 | Sipila et al. |
| 7,277,527 B2 | 10/2007 | Gallagher |
| 7,298,817 B2 | 11/2007 | Chen et al. |
| 7,342,995 B2 | 3/2008 | Sato et al. |
| 7,356,114 B2 | 4/2008 | Kataoka et al. |
| 7,375,359 B1 | 5/2008 | Grodzins |
| 7,409,037 B2 | 8/2008 | Puusaari et al. |
| 7,410,804 B2 | 8/2008 | Wendelbo et al. |
| 7,424,093 B2 | 9/2008 | Fukai et al. |
| 7,428,293 B2 | 9/2008 | Fukai et al. |
| 7,430,273 B2 | 9/2008 | Yellepeddi |
| 7,430,274 B2 | 9/2008 | Connors et al. |
| 7,436,926 B2 | 10/2008 | Matoba et al. |
| 7,440,541 B2 | 10/2008 | Hubbard-Nelson et al. |
| 7,443,951 B2 | 10/2008 | Kenning et al. |
| 7,515,685 B2 | 4/2009 | Iwamoto et al. |
| 7,518,722 B2 | 4/2009 | Julian et al. |
| 7,535,989 B2 | 5/2009 | Russell et al. |
| 7,587,025 B2 | 9/2009 | Fukai et al. |
| 7,623,621 B1 | 11/2009 | Schramm, Jr. |
| 7,623,625 B2 | 11/2009 | Boyden et al. |
| 7,627,088 B2 | 12/2009 | Matoba et al. |
| 7,634,053 B2 | 12/2009 | Matoba |
| 7,634,054 B2 | 12/2009 | Matoba et al. |
| 7,652,765 B1 | 1/2010 | Geshwind et al. |
| 7,653,174 B2 | 1/2010 | Mazor et al. |
| 7,657,414 B2 | 2/2010 | Zamora et al. |
| 7,680,243 B2 | 3/2010 | Yokhin et al. |
| 7,680,248 B2 | 3/2010 | Matoba |
| 7,688,942 B2 | 3/2010 | Klein |
| 7,763,820 B1 | 7/2010 | Sommer, Jr. et al. |
| 7,796,726 B1 | 9/2010 | Gendreau et al. |
| 7,916,834 B2 | 3/2011 | Piorek et al. |
| 7,970,101 B2 | 6/2011 | Sakai et al. |
| 7,978,820 B2 | 7/2011 | Kharchenko et al. |
| 7,983,386 B2 | 7/2011 | Yellepeddi et al. |
| 8,000,439 B2 | 8/2011 | Matoba |
| 8,018,586 B2 | 9/2011 | Genio et al. |
| 8,064,570 B2 | 11/2011 | Tannian et al. |
| 8,068,583 B2 | 11/2011 | Matoba et al. |
| 8,154,732 B2 | 4/2012 | Bodkin et al. |
| 8,155,268 B2 | 4/2012 | Pesce et al. |
| 8,238,515 B2 | 8/2012 | Birnbaum et al. |
| 8,380,541 B1 | 2/2013 | Holmes |
| 8,408,789 B2 | 4/2013 | Takahara |
| 8,494,113 B2 | 7/2013 | Grodzins |
| 8,515,720 B2 | 8/2013 | Koutsabeloulis et al. |
| 8,548,121 B2 | 10/2013 | Sakai |
| 8,550,710 B2 | 10/2013 | Kishida et al. |
| 8,582,717 B2 | 11/2013 | Ohzawa |
| 8,611,493 B2 | 12/2013 | Hasegawa et al. |
| 8,693,625 B2 | 4/2014 | Dugas et al. |
| 8,787,523 B2 | 7/2014 | Sackett |
| 8,793,111 B2 | 7/2014 | Tilke et al. |
| 8,835,857 B2 | 9/2014 | Eggert |
| 8,855,809 B2 | 10/2014 | Spencer et al. |
| 8,922,783 B2 | 12/2014 | Bodkin |
| 8,982,338 B2 | 3/2015 | Hamilton et al. |
| 9,057,685 B2 | 6/2015 | Allen et al. |
| 9,360,367 B2 | 6/2016 | Day et al. |
| 9,415,392 B2 | 8/2016 | Ismagilov et al. |
| 9,449,781 B2 | 9/2016 | Yun et al. |
| 9,476,810 B2 | 10/2016 | Gottlieb |
| 9,696,260 B2 | 7/2017 | Motto-Ros et al. |
| 9,756,219 B2 | 9/2017 | Konno et al. |
| 9,810,649 B2 | 11/2017 | Takahara et al. |
| 9,939,381 B1 | 4/2018 | Kimmel et al. |
| 10,041,833 B1 | 8/2018 | Chirayath |
| 10,207,296 B2 | 2/2019 | Garcia et al. |
| 10,242,126 B2 | 3/2019 | Zhdanov |
| 10,247,683 B2 | 4/2019 | Yun et al. |
| 10,295,486 B2 | 5/2019 | Yun et al. |
| 10,429,238 B2 | 10/2019 | Inoue et al. |
| 10,473,598 B2 | 11/2019 | Ogata et al. |
| 10,570,732 B2 | 2/2020 | Lawie et al. |
| 10,634,628 B2 | 4/2020 | Kasper et al. |
| 10,800,315 B2 | 10/2020 | Kanck et al. |
| 10,823,688 B2 | 11/2020 | Akiyama et al. |
| 10,948,435 B2 | 3/2021 | Furukawa |
| 10,983,062 B2 | 4/2021 | Özcan et al. |
| 11,037,283 B2 | 6/2021 | Jang et al. |
| 11,120,540 B2 | 9/2021 | Mairhofer |
| 11,320,384 B2 | 5/2022 | Grof et al. |
| 11,333,649 B2 | 5/2022 | Lalović |
| 11,352,879 B2 | 6/2022 | Li et al. |
| 11,519,868 B2 | 12/2022 | Verboomen et al. |
| 11,592,407 B2 | 2/2023 | Segal et al. |
| 11,733,185 B2 | 8/2023 | Ogata et al. |
| 12,181,429 B2 | 12/2024 | Pitta' et al. |
| 2003/0127776 A1 | 7/2003 | Carlson et al. |
| 2005/0090019 A1 | 4/2005 | Wendelbo et al. |
| 2005/0165555 A1 | 7/2005 | Jackson |
| 2005/0216197 A1 | 9/2005 | Zamora et al. |
| 2006/0038997 A1 | 2/2006 | Julian et al. |
| 2010/0106456 A1 | 4/2010 | Genio et al. |
| 2010/0185427 A1 | 7/2010 | Tilke et al. |
| 2011/0246154 A1 | 10/2011 | Koutsabeloulis et al. |
| 2013/0179130 A1 | 7/2013 | Zhandov |

(56) References Cited

U.S. PATENT DOCUMENTS

| | | | |
|---|---|---|---|
| 2014/0029004 A1 | 1/2014 | Bodkin | |
| 2014/0048972 A1 | 2/2014 | Gottlieb | |
| 2014/0183607 A1 | 7/2014 | Liu | |
| 2014/0204377 A1 | 7/2014 | Day et al. | |
| 2014/0379317 A1 | 12/2014 | Sanden et al. | |
| 2015/0163378 A1 | 6/2015 | Konno et al. | |
| 2015/0226673 A1* | 8/2015 | Motto-Ros | G01J 3/0218 |
| | | | 356/318 |
| 2015/0253263 A1 | 9/2015 | Feser et al. | |
| 2017/0074652 A1 | 3/2017 | Send et al. | |
| 2017/0321546 A1 | 11/2017 | Lawie et al. | |
| 2018/0073923 A1 | 3/2018 | Inoue et al. | |
| 2018/0275068 A1 | 9/2018 | Ozcan et al. | |
| 2018/0347354 A1 | 12/2018 | Li et al. | |
| 2020/0184624 A1 | 6/2020 | Jang et al. | |
| 2020/0193587 A1 | 6/2020 | Mairhofer | |
| 2022/0397517 A1 | 12/2022 | McQuilkin et al. | |

FOREIGN PATENT DOCUMENTS

| | | |
|---|---|---|
| CA | 2693247 A1 | 8/2010 |
| DE | 102007016612 A1 | 10/2008 |
| DE | 102020132736 A1 | 6/2021 |
| EP | 2270479 A2 | 1/2011 |
| EP | 3062096 B1 | 8/2016 |
| WO | 2015189286 A1 | 12/2015 |
| WO | 2019/213765 A1 | 11/2019 |
| WO | 2019218051 A1 | 11/2019 |
| WO | 2019236339 A1 | 12/2019 |
| WO | 2021176419 A1 | 9/2021 |
| WO | 2022266779 A1 | 12/2022 |

OTHER PUBLICATIONS

Barton. "Discrimination of Natural Fractures from Drilling- Induced Wellbore Failures in Wellbore Image Data—Implications for Reservoir Permeability". Society of Petroleum Engineers. Feb. 1, 2000. doi:10.2118/58993-MS, 8 pages.

Fox, et al. "Applications of hyperspectral mineralogy for geoenvironmental characterisation", Minerals Engineering, vol. 107, Sep. 18, 2016 (Sep. 18, 2016), ISSN: 0892-6875, DOI: 10.1016/J. MINENG.2016.11.008, Sep. 18, 2016, 15 pages.

ISA/CA, International Search Report, re PCT International Patent Application No. PCT/CA2022/051025, Aug. 8, 2022, 4 pages.

Kooima, et al. "Planetary-scale terrain composition." IEEE Transactions on Visualization and Computer Graphics 15.5 (2009): 719-733, Apr. 24, 2009, 15 pages.

Lypaczewski, et al. "Using hyperspectral imaging to vector towards mineralization at the Canadian Malartic gold deposit, Quebec, Canada", Ore Geology Reviews, Elsevier, Amsterdam, NL, vol. 111, ISSN: 0169-1368, DOI: 10.1016/J.OREGEOREV.2019. 102945, May 25, 2019, 15 pages.

McCarthy, et al. "A GIS-based borehole data management and 3D visualization system." Computers & Geosciences 32.10 (2006): 1699-1708, Nov. 30, 2006, 11 pages.

Extended European Search Report in European App. No. 22826945. 2, dated Apr. 14, 2025, 12 pages.

Paradis, et al. "ECORE: A New Fast Automated Quantitative Mineral and Elemental Core Scanner", Minerals, vol. 11, No. 8, Aug. 10, 2021 (Aug. 10, 2021), p. 859, XP093106816, DOI: 10.3390/min11080859 Retrieved from the Internet: URL:https:// www.mdpi.com/2075-163X/ 11/8/859#:~:text=The%20new% 20ECORE%20can%20scan,properties%20of%20the%20full% 20tray, 16 pages.

Rifai, et al., "Emergences of New Technology for Ultrafast Automated Mineral Phase Identification and Quantitative Analysis Using the CORIOSITY Laser-Induced Breakdown Spectroscopy (LIBS) System", Minerals, vol. 10, No. 10, Oct. 16, 2020 (Oct. 16, 2020), p. 918, XP093266577, ISSN: 2075-163X, DOI: 10.3390/ min10100918, 19 pages.

Rifai, et al., "Ultrafast Elemental Mapping of Platinum Group Elements and Mineral Identification in Platinum-Palladium Ore Using Laser Induced Breakdown Spectroscopy", Minerals, vol. 10, No. 3, Feb. 25, 2020 (Feb. 25, 2020), p. 207, XP093205412, ISSN: 2075-163X, DOI: 10.3390/min10030207 Retrieved from the Internet: URL:https://www.mdpi.com/2075-163X/10/3/207/pdf &, 10 pages.

International Search Report in International App. No. PCT/CA2025/ 051346 mailed Jan. 12, 2026, 4 pages.

Written Opinion in International App. No. PCT/CA2025/051346 dated Jan. 8, 2026, 6 pages.

* cited by examiner

LASER INDUCED BREAKDOWN SPECTROSCOPY FOR GEOLOGICAL ANALYSIS

RELATED APPLICATION DATA

The present application is a continuation of international PCT patent application no. PCT/CA2022/051025, filed Jun. 25, 2022, which claims priority to, and the benefit of, provisional U.S. patent application No. 63/215,005, filed Jun. 25, 2021, the content of both of these documents being incorporated herein by reference.

TECHNICAL FIELD

The present disclosure relates to laser induced breakdown spectroscopy, and more particularly to laser induced breakdown spectroscopy (LIBS) devices for analysis of geological and related samples.

BACKGROUND

Laser induced breakdown spectroscopy (LIBS) involves the use of focused high energy laser pulses to ablate small samples (in the nanogram to picogram ranges) to form plasma. The plasma generated by sample ablation is analyzed with a spectrometer which generates characteristic emission lines of individual elements present in the plasma.

One challenge in the efficient and/or otherwise effective use of LIBS in the analysis of geological samples is a high variability in the quality of laser sparks and resulting plasma. This can be addressed by, for example, emitting and measuring multiple laser pulses for each sample point and using the best measurements. Observation of the laser light path may be used to provide focus and positional (or spatial) accuracy of the laser. However, it becomes difficult to focus the laser and align the observation mechanism with the surface under ablation when the surface has higher variability and/or the acquisition speed increases (for example, to support continuous scanning or imaging).

For at least reasons given above, there is a need for improved laser induced breakdown spectroscopy devices and related methods.

SUMMARY

The present disclosure provides methods, devices, and systems for laser induced breakdown spectroscopy, including a method for laser induced breakdown spectroscopy using a laser induced breakdown spectroscopy scanning head, and a scanning system for geological cores. The laser induced breakdown spectroscopy devices described herein may be used for line, point, and/or imaging operations. The present disclosure provides also provides an integrated laser focusing system with other components described herein.

In the method, a scanning table having a geological core disposed upon a scanning surface thereof is moved from a start position to an end position for each position in a plurality of positions of the scanning table corresponding to a region of interest of the geological core. At each position, laser ablation is performed on the exposed surface of the geological core using an oscillating planar focus laser. Contemporaneously with performing laser ablation on the exposed surface of the geological core, spectroscopy is permitted on the emitted light received by a fiber optic receiver (or other optical receiver) sharing an optical path with the oscillating planar focus laser. The oscillating planar focus laser may focus laser light to a focus point, where the focus point is moved about two axes to define a focal plane.

In accordance with a first aspect of the present disclosure, a method for laser induced breakdown spectroscopy (LIBS) using a LIBS scanning head, the LIBS scanning head comprising an oscillating planar focus laser for performing laser ablation on a geological core, thereby forming plasma, and a fiber optic receiver for receiving light emitted from an ablation site on the geological core, the oscillating planar focus laser and fiber optic receiver having a shared optical path with a focus lens of the LIBS scanning head at one end, the LIBS scanning head being adapted to two-dimensionally rotate the shared optical path to control a position of a focal plane of the LIBS scanning head, the LIBS scanning head being mounted relative to a moveable scanning table, the LIBS scanning head being mounted to be moveable (e.g., vertically) relative to a scanning surface of the scanning table, the method comprising: (i) moving a scanning table with a geological core disposed upon a scanning surface thereof to a table position in a plurality of table positions of the scanning table of a scanning path, wherein the plurality of table positions correspond to a region of interest of the geological core; (ii) positioning a focal plane of the LIBS scanning head in accordance with the table position; (iii) performing laser ablation on the geological core and forming plasma using the oscillating planar focus laser of the LIBS scanning head; and (iv) contemporaneously with performing laser ablation on geological core, performing spectroscopy on the emitted light received by the fiber optic receiver; wherein steps (i) to (iv) are performed for each table position in the plurality of table positions.

In some or all examples of the first aspect, the method is performed sequentially from a start position to an end position.

In some or all examples of the first aspect, the method comprises: receiving three-dimensional (3D) coordinates of the geological core; determining 3D coordinates of an exposed surface of the geological core relative to a reference based on a 3D coordinates and orientation of the focal plane of the LIBS scanning head relative to the reference, and 3D coordinates of a scanning surface of the scanning table relative to the reference; and determining the scanning path by determining, for each position in a plurality of positions of the scanning table corresponding to the region of interest of the geological core, a curve of intersection of the focal plane of the LIBS scanning head and the 3D coordinates of the exposed surface of the geological core in the region of interest.

In some or all examples of the first aspect, the scanning path defines a vertical direction and distance between the LIBS scanning head and the exposed surface of the geological core when located on the scanning surface of the scanning table, and a 3D orientation of the focal plane of the LIBS scanning head.

In some or all examples of the first aspect, the focal plane of the LIBS scanning head in accordance with the scanning path comprises one or more of: raising or lowering the LIBS scanning head relative to the scanning surface of the scanning table to correspond to the vertical direction and distance defined by the scanning path for the respective position of the scanning table; and rotating the shared optical path of the LIBS scanning head so that the position of the focal plane of the LIBS scanning head corresponds to the 3D orientation of the focal plane of the LIBS scanning head defined by the scanning path for the respective position of the scanning table.

In some or all examples of the first aspect, the method comprises: obtaining sensor data for one or more scans of the geological core obtained via one or more other sensors; and determining the region of interest of the geological core based on the sensor data for one or more scans of the geological core obtained via the one or more other sensors.

In some or all examples of the first aspect, determining the region of interest comprises: determining, from the sensor data, one or a combination of a presence of one or more minerals in the geological core, a presence of one or more elements in the geological core, a presence of sulphides in the geological core, alterations in the geological core, or a rock quality of the geological core; and determining the region of interest based of the geological core based on one or a combination of a presence of one or more minerals in the geological core, a presence of one or more elements in the geological core, a presence of sulphides in the geological core, alterations in the geological core, or a rock quality of the geological core.

In some or all examples of the first aspect, the one or more other sensors comprise one or more hyperspectral cameras, one or more RGB (red, green, blue) cameras, one or more x-ray fluorescence (XRF) spectrometers, a magnetic susceptibility sensor, or a combination thereof.

In some or all examples of the first aspect, the region of interest is a dynamically selected region of interest.

In some or all examples of the first aspect, the region of interest is a whole exposed surface of the geological core.

In some or all examples of the first aspect, the scanning path depends on a scanning speed of the scanning head and a speed at which the scanning table moves.

In some or all examples of the first aspect, the method comprises: providing the LIBS scanning head.

In some or all examples of the first aspect, the method comprises: generating a two-dimensional (2D) projection of spectra readings of the geological core generated by the spectroscopy.

In some or all examples of the first aspect, the method comprises: overlaying the 2D projection of the spectra readings upon a base digital image of the geological core.

In some or all examples of the first aspect, the base digital image is a hyperspectral image, a natural light (or RGB) photographic image, or an XRF image.

In accordance with a second aspect of the present disclosure, there is provided a laser induced breakdown spectroscopy (LIBS) scanning head, comprising: a housing; an oscillating planar focus laser received in the housing, the oscillating planar focus laser having a laser light emission path along which laser light is directed; a fiber optic receiver (or other optical receiver) received in the housing, the fiber optic receiver have a fiber optic output port, the fiber optic receiver having a light reception path along which observed natural light is received, wherein the light reception path is perpendicular to the laser light emission path; a dichroic element received in the housing and oriented at 45 degrees relative to the light reception path and the laser light emission path, wherein the dichroic element may be configured to reflect laser light emitted by the oscillating planar focus laser and transmit natural light for reception by the fiber optic receiver; a first focus lens received in the housing for focusing the reflect laser light emitted by the oscillating planar focus laser and receiving natural light, wherein a shared optical path is provided between the oscillating planar focus laser and fiber optic receiver between the dichroic element and the first focus lens; and a pair of rotatable scanning mirrors received in the housing and located between the dichroic element and the first focus lens, the pair of scanning mirrors being adapted to rotate the shared optical path about two axes to define a focal plane of the LIBS scanning head.

In some or all examples of the second aspect, the LIBS scanning head comprises: a second focus lens received in the housing and located between the dichroic element and the fiber optic receiver, the second focus lens focuses received natural light prior to reception by the fiber optic receiver.

In some or all examples of the second aspect, the LIBS scanning head comprises: a fiber optic splitter coupled to the fiber optic receiver, the fiber optic splitter having a plurality of fiber optic output ports; or multi-furcated fiber.

In some or all examples of the second aspect, the first focus lens is an F-Theta lens.

In accordance with a third aspect of the present disclosure, there is provided a scanning system for geological cores, comprising: a moveable scanning table have a scanning surface; a laser induced breakdown spectroscopy (LIBS) scanning head mounted relative to a scanning table to be moveable (e.g., vertically) relative to a scanning surface of the scanning table, the LIBS scanning head comprising: a housing; an oscillating planar focus laser received in the housing, the oscillating planar focus laser having a laser light emission path along which laser light is directed; a fiber optic receiver (or other optical receiver) received in the housing, the fiber optic receiver have a fiber optic output port, the fiber optic receiver having a light reception path along which observed natural light is received, wherein the light reception path is perpendicular to the laser light emission path; a dichroic element received in the housing and oriented at 45 degrees relative to the light reception path and the laser light emission path, wherein the dichroic element may be configured to reflect laser light emitted by the oscillating planar focus laser and transmit natural light for reception by the fiber optic receiver; a first focus lens received in the housing for focusing the laser light emitted by the oscillating planar focus laser and receiving natural light, wherein a shared optical path is provided between the oscillating planar focus laser and fiber optic receiver between the dichroic element and the first focus lens; and a pair of rotatable scanning mirrors received in the housing and located between the dichroic element and the first focus lens, the pair of scanning mirrors being adapted to rotate the shared optical path about two axes to define a focal plane of the LIBS scanning head; a controller for controlling the moveable scanning table and controlling the LIBS scanning head.

In some or all examples of the third aspect, the scanning system comprises: a second focus lens received in the housing and located between the dichroic element and the fiber optic receiver, the second focus lens focuses received natural light prior to reception by the fiber optic receiver.

In some or all examples of the third aspect, the first focus lens is an F-Theta lens.

In some or all examples of the third aspect, the scanning system comprises: a spectrometer coupled to the fiber optic receiver, the spectrometer selected from the group consisting of a visible light spectrometer, ultraviolet light spectrometer, and infrared light spectrometer.

In some or all examples of the third aspect, the scanning system comprises: a fiber optic splitter coupled to the fiber optic receiver, the fiber optic splitter having a plurality of fiber optic output ports; or multi-furcated fiber.

In some or all examples of the third aspect, the scanning system comprises: a plurality of spectrometers coupled to the fiber optic splitter, the spectrometers selected from the group consisting of a visible light spectrometer, ultraviolet light spectrometer, and infrared light spectrometer.

In some or all examples of the third aspect, the spectrometers are coupled to the controller, wherein the spectrometers output spectral data to the controller, wherein the controller is configured to store the spectral data received from the spectrometers.

In some or all examples of the third aspect, the controller is configured to: (i) cause the scanning table to move with the geological core disposed upon a scanning surface thereof to a table position in a plurality of table positions of the scanning table of a scanning path, wherein the plurality of table positions correspond to a region of interest of the geological core; (ii) cause a focal plane of the LIBS scanning head to be positioned in accordance with the table position; (iii) cause laser ablation to be performed on the geological core using the oscillating planar focus laser of the LIBS scanning head; and (iv) contemporaneously with performing laser ablation on geological core, cause spectroscopy to be performed on the emitted light received by the fiber optic receiver; wherein steps (i) to (iv) are performed for each table position in the plurality of table positions.

In some or all examples of the third aspect, the controller is configured to: receive three-dimensional (3D) coordinates of the geological core; determine 3D coordinates of an exposed surface of the geological core relative to a reference based on a 3D coordinates and orientation of the focal plane of the LIBS scanning head relative to the reference, and 3D coordinates of a scanning surface of the scanning table relative to the reference; determine a scanning path for the LIBS scanning head by determining, for each position in a plurality of positions of the scanning table corresponding to a region of interest of the geological core, a curve of intersection of the focal plane of the LIBS scanning head and the 3D coordinates of the exposed surface of the geological core in the region of interest; cause the scanning table to move from a start position to an end position for each position in the plurality of positions of the scanning table corresponding to the region of interest of the geological core; during the movement of the scanning table from the start position to the end position, at each position in the plurality of positions of the scanning table corresponding to the region of interest of the geological core: cause the focal plane of the LIBS scanning head to be positioned in accordance with the scanning path; cause laser ablation to be performed on the exposed surface of the geological core located on the scanning surface of the scanning table using the oscillating planar focus laser of the LIBS scanning head; and contemporaneously with performing laser ablation on the exposed surface of the geological core, cause spectroscopy to be performed on the emitted light received by the spectrometers.

In accordance with another aspect of the present disclosure, there is provided a method for laser induced breakdown spectroscopy (LIBS) using a LIBS scanning head, the LIBS scanning head comprising an oscillating planar focus laser for performing laser ablation on a geological core and a fiber optic receiver (or other optical receiver) for receiving light emitted from an ablation site on the geological core, the oscillating planar focus laser and fiber optic receiver having a shared optical path with a focus lens of the LIBS scanning head at one end, the LIBS scanning head being adapted to two-dimensionally rotate the shared optical path to control a position of a focal plane of the LIBS scanning head, the LIBS scanning head being mounted relative to a moveable scanning table, the LIBS scanning head being mounted to be moveable (e.g., vertically) relative to a scanning surface of the scanning table, comprising: receiving three-dimensional (3D) coordinates of the geological core; determining 3D coordinates of an exposed surface of the geological core relative to a reference based on a 3D coordinates and orientation of the focal plane of the LIBS scanning head relative to the reference, and 3D coordinates of a scanning surface of the scanning table relative to the reference; determining a scanning path for the LIBS scanning head by determining, for each position in a plurality of positions of the scanning table corresponding to a region of interest of the geological core, a curve of intersection of the focal plane of the LIBS scanning head and the 3D coordinates of the exposed surface of the geological core in the region of interest; moving the scanning table from a start position to an end position for each position in the plurality of positions of the scanning table corresponding to the region of interest of the geological core; during the movement of the scanning table from the start position to the end position, at each position in the plurality of positions of the scanning table corresponding to the region of interest of the geological core: positioning the focal plane of the LIBS scanning head in accordance with the scanning path; performing laser ablation on the exposed surface of the geological core located on the scanning surface of the scanning table, thereby forming plasma, using the oscillating planar focus laser of the LIBS scanning head; and contemporaneously with performing laser ablation on the exposed surface of the geological core, performing spectroscopy on the emitted light received by the fiber optic receiver.

In accordance with a further aspect of the present disclosure, there is provided a computing device comprising one or more processors and a memory. The memory having tangibly stored thereon executable instructions for execution by the one or more processors. The executable instructions, in response to execution by the one or more processors, cause the computing device to perform at least parts of the methods described above and herein.

In accordance with a further aspect of the present disclosure, there is provided a non-transitory machine-readable medium having tangibly stored thereon executable instructions for execution by one or more processors. The executable instructions, in response to execution by the one or more processors, cause the one or more processors to perform at least parts of the methods described above and herein.

Other aspects and features of the present disclosure will become apparent to those of ordinary skill in the art upon review of the following description of specific implementations of the application in conjunction with the accompanying figures.

DETAILED DESCRIPTION OF EXAMPLE EMBODIMENTS

Figures 1A, 1B, 1C, 1D:
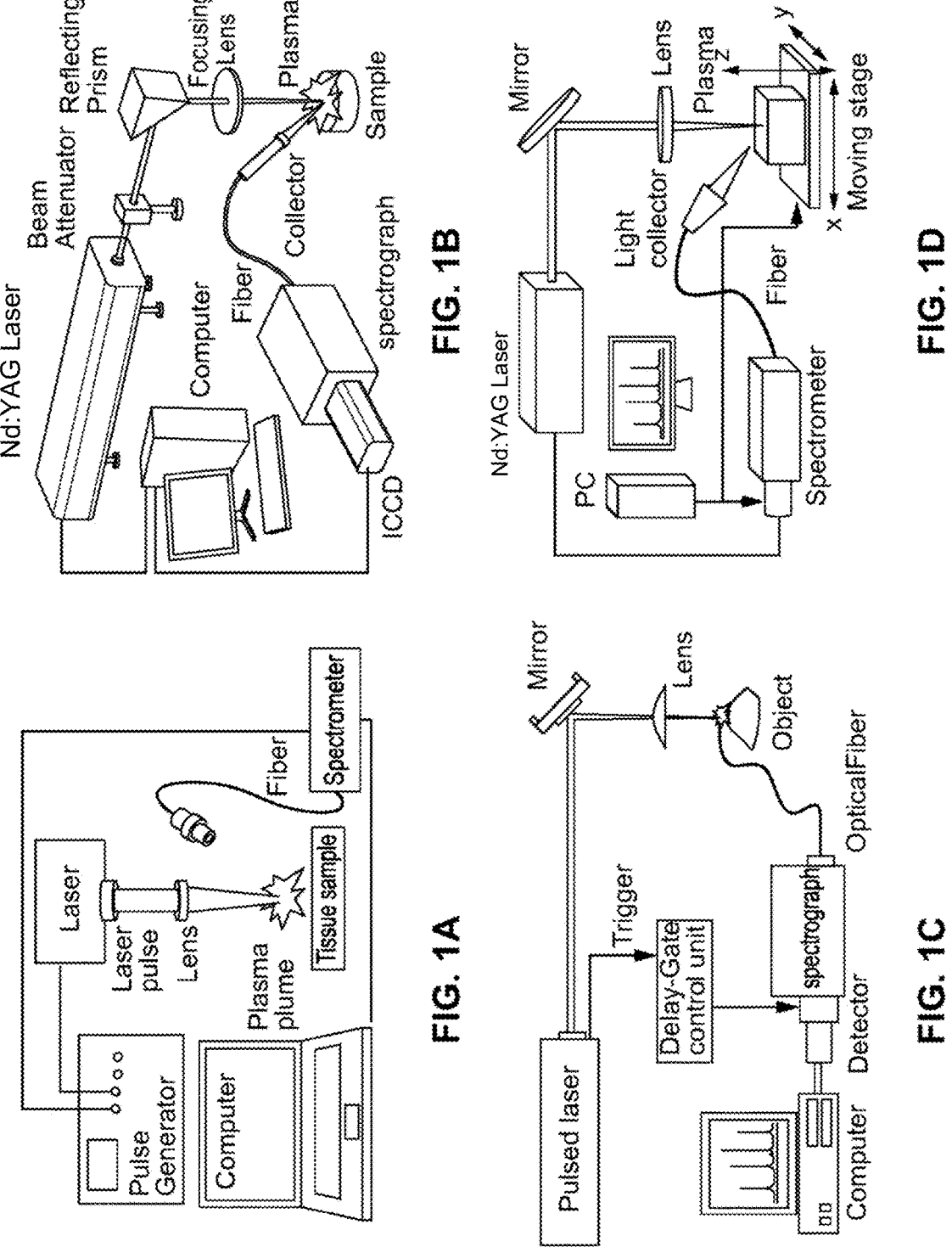
FIGS. 1A, 1B, 1C and 1D illustrate conventional LIBS setups for stationary samples.

The present disclosure is made with reference to the accompanying drawings, in which embodiments are shown. However, many different embodiments may be used, and thus the description should not be construed as limited to the embodiments set forth herein. Rather, these embodiments are provided so that this application will be thorough and complete. Wherever possible, the same reference numbers are used in the drawings and the following description to refer to the same elements, and prime notation is used to indicate similar elements, operations or steps in alternative embodiments. Separate boxes or illustrated separation of functional elements of illustrated systems and devices does not necessarily require physical separation of such functions, as communication between such elements may occur by way of messaging, function calls, shared memory space, and so on, without any such physical separation. As such, functions need not be implemented in physically or logically separated platforms, although such functions are illustrated separately for ease of explanation herein. Different devices may have different designs, such that although some devices implement some functions in fixed function hardware, other devices may implement such functions in a programmable processor with code obtained from a machine-readable medium. Lastly, elements referred to in the singular may be plural and vice versa, except wherein indicated otherwise either explicitly or inherently by context.

For the purpose of the present disclosure, the term "real-time" means that a computing operation or process is completed within a relatively short maximum duration, typically milliseconds or microseconds, fast enough to affect the environment in which the computing operation or process occurs, such as the inputs to a computing system. The term "dynamic" refers to a result dependent on the value of a set of one or more variables, wherein the result is or may be determined in real-time in response to detection of a trigger. Geometric terms such as parallel, perpendicular, straight and cylindrical are used in the present disclosure. It should be understood that some variance and tolerance are permitted within the context of these terms except wherein indicated otherwise either explicitly or inherently by context.

Within the present disclosure, the terms "positional" and "spatial" are used interchangeably.

Laser Induced Breakdown Spectroscopy for Geological Analysis

FIGS. 1A, 1B, 1C and 1D illustrate conventional LIBS setups for stationary samples. The examples of LIBS setups shown in FIGS. 1A-1D are useful for analyzing lab samples, and particularly small samples. It can be seen that in the shown examples that light collecting optical fibers are directed towards the samples along optical paths separate from the focused laser light paths. For very regular and/or stationary surfaces, combined focus and positional accuracy of the laser and collecting light path can be easily achieved. However, as the surface variability increases and/or the desired acquisition speed increases (i.e., to support continuous scanning or imaging), it becomes more challenging to focus the laser, and to ensure that the light transmission and collection paths are properly correlated.

Figure 2:
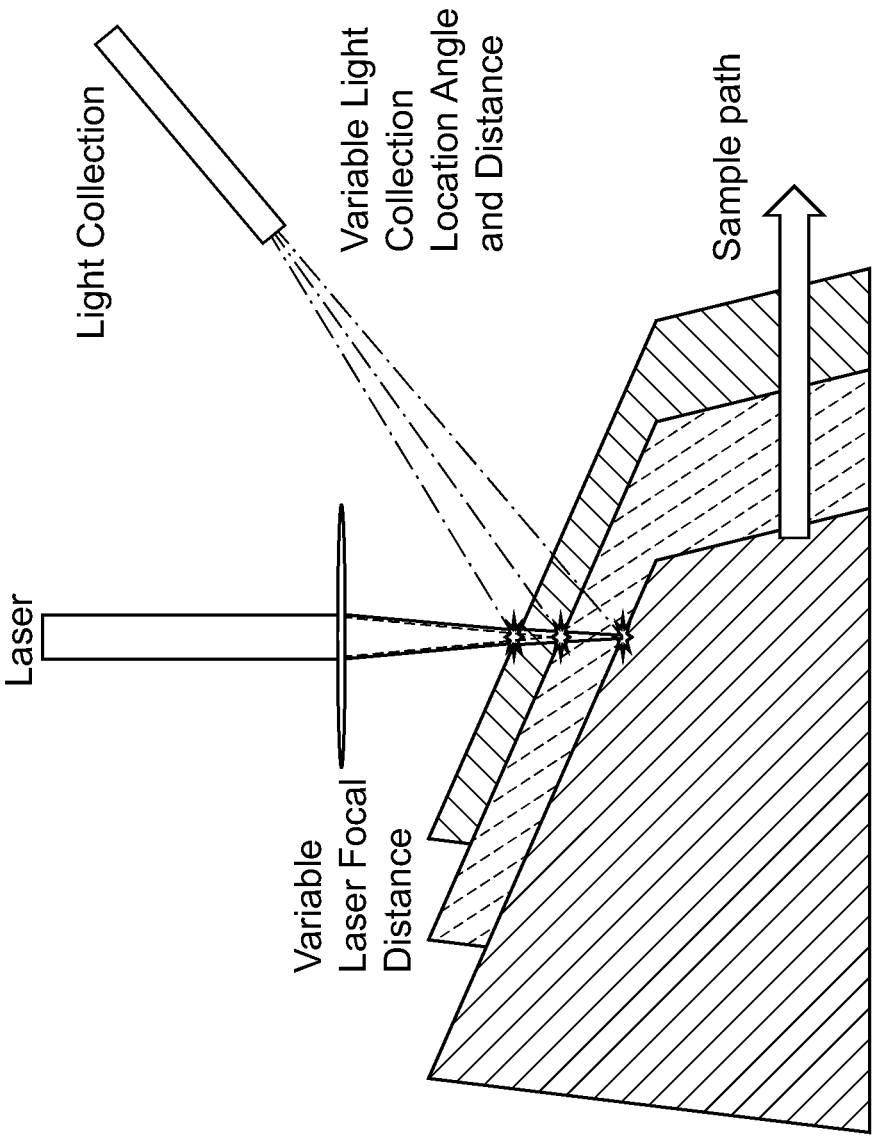
FIG. 2 illustrates an example of a laser ablation setup.

For applications related to analysis of geological samples such as drilling cores, it can be desirable to effectively apply laser induced breakdown spectroscopy (LIBS) to topographically-variable surfaces at high speeds, for example by inducing relative motion between the LIBS device and the core or other sample. FIG. 2 illustrates an example of a laser ablation setup and the challenges of LIBS for geological samples. As for example can be seen in FIG. 2, this can give rise to control issues related to laser pulse focus and related light collection accuracy.

The present disclosure provides methods, devices, and systems for controlling the laser direction and/or focal distance by, for example, providing for the adjustment of both beam direction and focus in multiple directions and/or over a range of distances as data is collected. Alternatively, or in addition, the present disclosure provides methods, devices, and systems for controlling light collection at desired points by configuring the optical collection path parallel and at least partially co-axial to the path of the laser transmission. Moreover, when for example improved precision in focus distance and location are desired to achieve improved signal quality for desired detection limits, the teachings of the present disclosure can provide for high speed mechanical and/or electro-optical focus and aim, including for example oscillation or other controlled motion of both the laser and data collection paths.

The present disclosure provides methods, devices, and systems that use oscillating and/or otherwise controllably directable laser or other ablation light sources and corresponding scan heads, designed to maintain laser focus across desired lines and/or horizontal planes. The present disclosure also provides methods, devices, and systems that use adapters for cameras and/or other photosensitive devices to allow the laser or other light source to share an optical path the cameras or other devices (for example, so that locations for which data is being collected is easily determined for monitoring, analysis and quality control (QC) purposes).

Figures 3A, 3B:
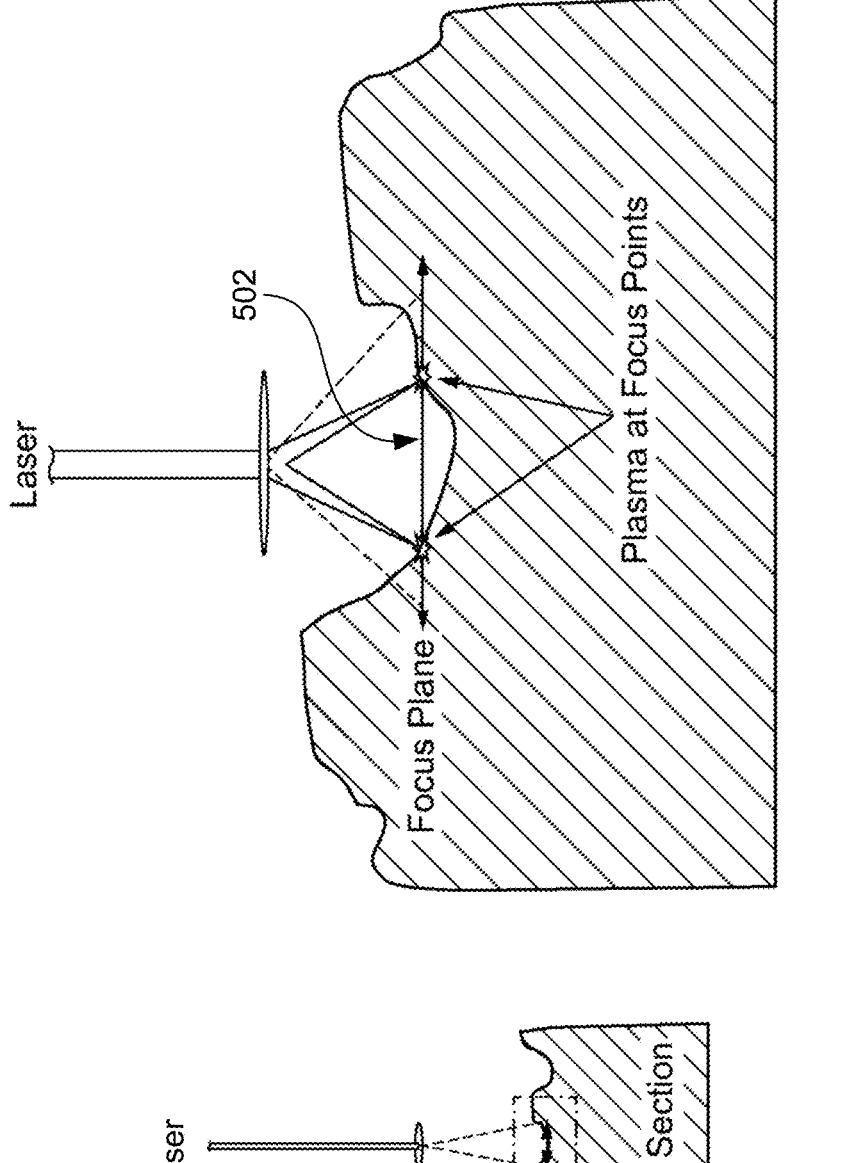
FIG. 3A is a schematic diagram illustrating the focal plane of an oscillating planar focus laser on a variable surface.
FIG. 3B is an enlarged view of the schematic diagram of FIG. 3A.

As shown for example in FIGS. 3A and 3B, the methods, devices, and systems of the present disclosure use an oscillating planar focus laser to ensure that for a variable surface, plasma generation at multiple focused points can be achieved, at least for points on a focal plane 502 (also known as a focus plane) lying within the bounds of the peaks and troughs of the core surface. In various embodiments this can be achieved by, for example using three-dimensional (3D) positional data (e.g., 3D coordinates) generated by a positional scanner such as a detection and ranging device (such as LiDAR (Light Detection and Ranging)) in addition to ablation light sources to calculate the nominal height of the geological core surface and adjusting the relative position of the scanning head.

Figures 4A, 4B, 4C:
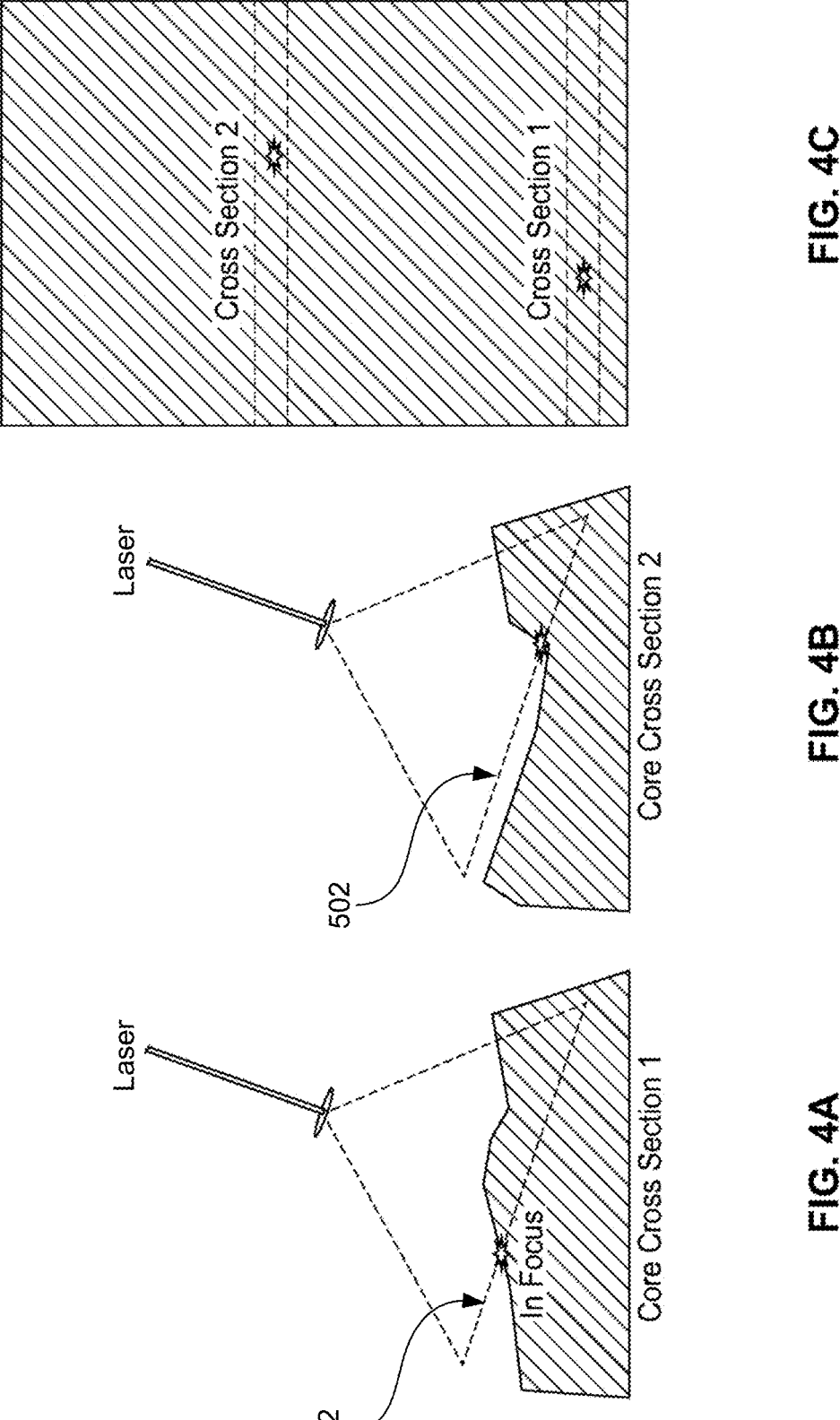
FIG. 4A illustrates the focal plane at a first cross section of a geological core having a variable surface.
FIG. 4B illustrates the focal plane at a second cross section of the geological core.
FIG. 4C illustrates a cross sectional map of the geological core created by the cross sections of FIGS. 4A and 4B.

FIGS. 4A-4C are a series of schematic diagrams illustrating how by tilting the focal plane 502 of a scanning laser relative to the notional surface of a geological core in accordance with the present disclosure, a large depth of field (e.g., wider depth of field) can be created for the instrument even though the depth of field of the laser itself is extremely small. FIG. 4A illustrates the focal plane 502 at a first cross section of a geological core having a variable surface and FIG. 4B illustrates the focal plane 502 at a second cross section of the geological core. FIG. 4C illustrates a cross sectional map of the geological core created by the two cross sections. The focal plane 502 of the laser can be angled such that at one or more points across the geological core there will be at least one intersection between the focal plane 502 and the geological core surface.

Figure 5:
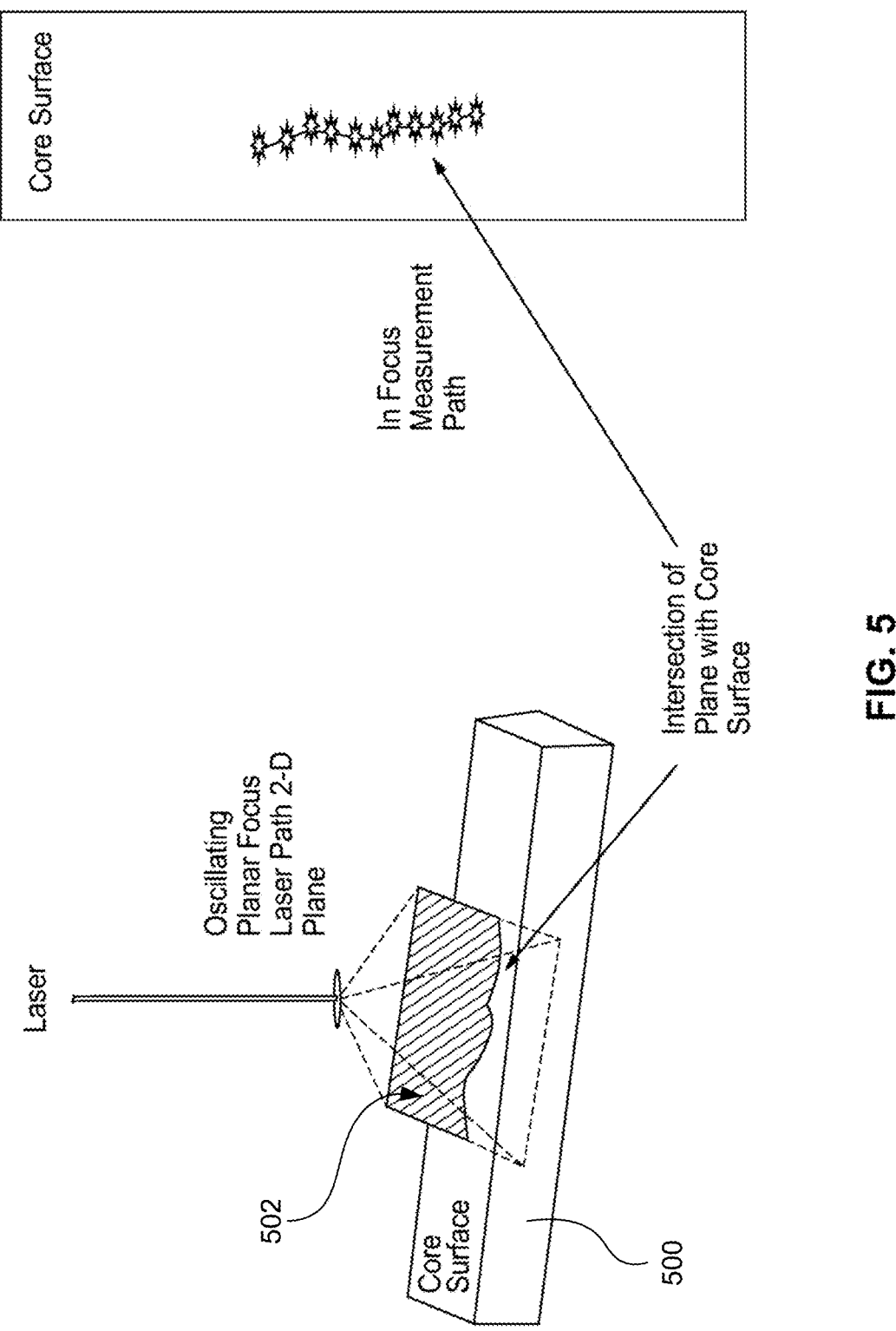
FIG. 5 is a schematic diagram illustrating how a focused path is created using an oscillating planar focus laser with an angled focal plane in accordance with example embodiments of the present disclosure.

FIG. 5 is a schematic diagram illustrating how a focused path is created using an oscillating planar focus laser with an angled focal plane 502 in accordance with example embodiments of the present disclosure. In particular, FIG. 5 shows how an angled two-dimensional plane 502 provides a line of focus across a geological core 500. This allows measurements to be taken at any axial points along a geological core 500 so long as extreme accuracy in the precise location of the data sample circumferentially across the geological core 500 is not required. Continuous scan lines of readings along one or more axes of the geological core 500 can therefore be created, although measurement paths may vary to some controllable extent across the width of the geological core 500 depending, for example on the average roughness of the geological core surface. Locational accuracy, for example along a circumference of the geological core 500, can be improved by a variety of methods, such as using metadata collected about scanning head and imager positions, orientations, and timing to re-construct precisely the location of each successful reading.

Figure 6:
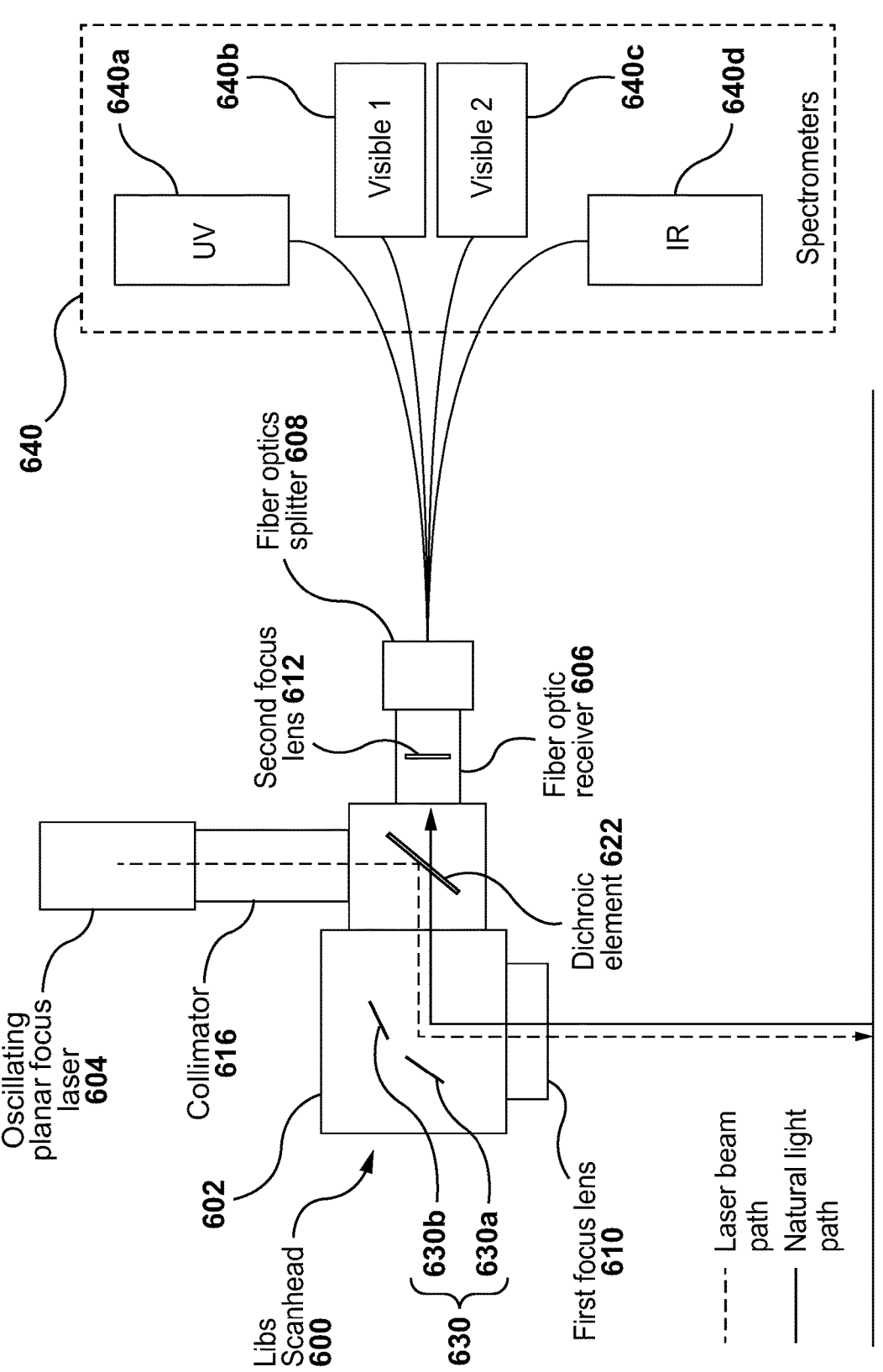
FIG. 6 is a schematic diagram of a LIBS scanning head in accordance with one embodiment of the present disclosure.
Figure 9:
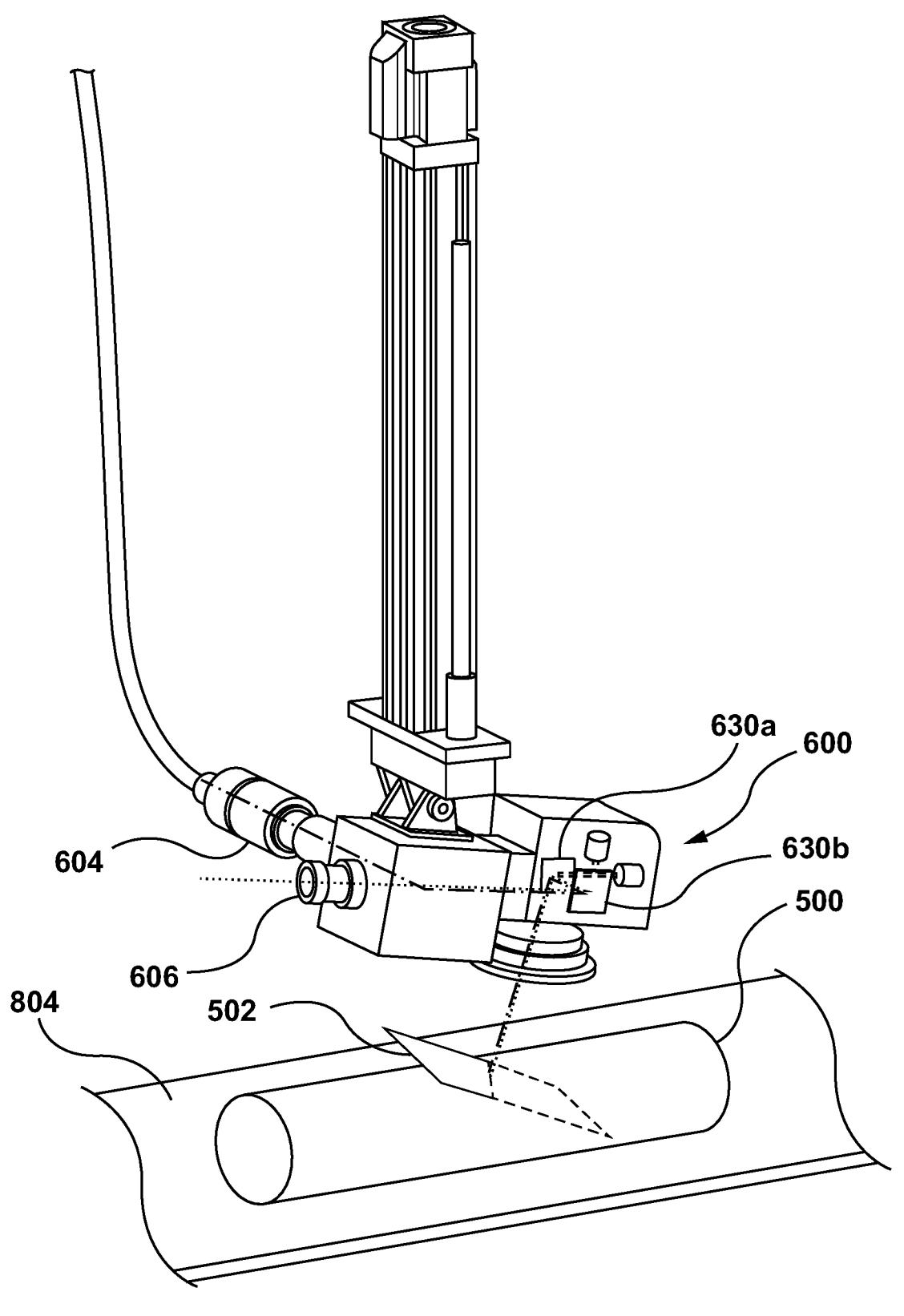
FIG. 9 is a perspective view of a LIBS scanning head of the scanning system of FIG. 8.

Referring to FIGS. 6 and 9, a LIBS scanning head 600 in accordance with one embodiment of the present disclosure. The LIBS scanning head 600 comprises a housing 602, an oscillating planar focus laser 604 received in the housing 602, and a fiber optic (light) receiver 606 received in the housing 602. The fiber optic receiver 606 may also be referred to as a fiber optic collector or fiber optic adapter which comprises fiber optic cable that receives light, such as reflected laser light from a laser ablation site. The oscillating planar focus laser 604 has a laser light emission path along which laser light is directed. The fiber optic receiver 606 has a light reception path along which observed natural light is received. The light reception path of the fiber optic receiver 606 is perpendicular to the laser light emission path of the oscillating planar focus laser 604 in this example.

In one example, the oscillating planar focus laser 604 is a fiber laser with an output pulse energy of up to 1 mJ and 20-50 ns pulses @20 kHz are performed in series from 2 to 10 pulses per shot. In an example, one shot with the oscillating planar focus laser 604 with spectrometer data acquisition and dead time takes 1-5 ms. Dead time can be used to perform another shot with the oscillating planar focus laser 604 because of poor plasma generation (which can be detected in data acquired during data acquisition for the shot, possibly automatically—poor plasma generation results in spectral data outside of a normal operating range) or data acquisition with another spectrometer can be performed. In one example, each shot with spectrometer data acquisition and dead time has a duration of 5 ms, with a scan line length of 25 mm, 50 experiments per line (an experiment every 0.5 mm), with a geological core length of about 1 m, resulting in a total scan time of 500 s with approximately 2,000 lines totaling 100,000 acquired spectra per geological core.

In this embodiment, a dichroic element 622 is mounted in the housing 602 and oriented at degrees relative to the light reception path and the laser light emission path. The dichroic element 622 is configured to reflect laser light emitted by the oscillating planar focus laser 604 and transmit natural light along the same, or substantially the same, path that the light was transmitted along for reception by the fiber optic receiver 606. The dichroic element 622 may be selected to reflect or transmit different wavelengths of interest. A collimator 616 is located between the oscillating planar focus laser 604 and the dichroic element 622.

A first focus lens 610 is received in the housing 602 for focusing the laser light emitted by the oscillating planar focus laser 604 and receiving natural light. In at least some examples, the first focus lens 610 is an F-Theta lens, also known as a scan objective or flat field objective lens. A shared optical path is provided between the oscillating planar focus laser 604 and fiber optic receiver 606 between the dichroic element and the first focus lens 610.

A pair of rotatable scanning mirrors 630, represented individually by references 630a and 630b respectively, are received in the housing 602 and located between the dichroic element 622 and the first focus lens 610. The pair of scanning mirrors 630 are adapted to two-dimensionally rotate the shared optical path to control a position of a focal plane of the LIBS scanning head 600. The positions of the scanning mirrors 630 are controlled by galvanometers. By controlling the voltage of a control signal transmitted to the galvanometers, the position of the scanning mirrors 630 is changed by causing the scanning mirrors rotating in a respective one of the x- and y-axes, collectively allowing the shared optical path to be changed (e.g., rotated) about two axes.

A second focus lens 612 is received in the housing 602 and located between the dichroic element 622 and the fiber optic receiver 606. The second focus lens 612 focuses received natural light prior to reception by the fiber optic receiver 606. The fiber optic receiver 606 may comprise another focus lens and/or collimator.

A fiber optic splitter 608 is coupled to the fiber optic receiver 606 via an output port thereof. The fiber optic splitter 608 has a plurality of fiber optic output ports. Alternatively, multi-furcated fiber may be used instead of a fiber optic splitter 608. Multi-furcated fiber consists of multiple fibers bundled together at one end and separated at the opposite end, thereby providing a plurality of fiber optic output ports. Each of the plurality of fiber optic output ports of the fiber optic splitter 608 or multi-furcated fiber is connected to a spectrometer 640. In the shown example, the spectrometers 640 comprise an ultraviolet light spectrometer 640a, a first visible (natural) light ultraviolet light spectrometer 640b, a second visible (natural) light ultraviolet light spectrometer 640c, and an infrared light spectrometer 640d. A greater or fewer number of spectrometers may be used in other examples.

Figure 7:
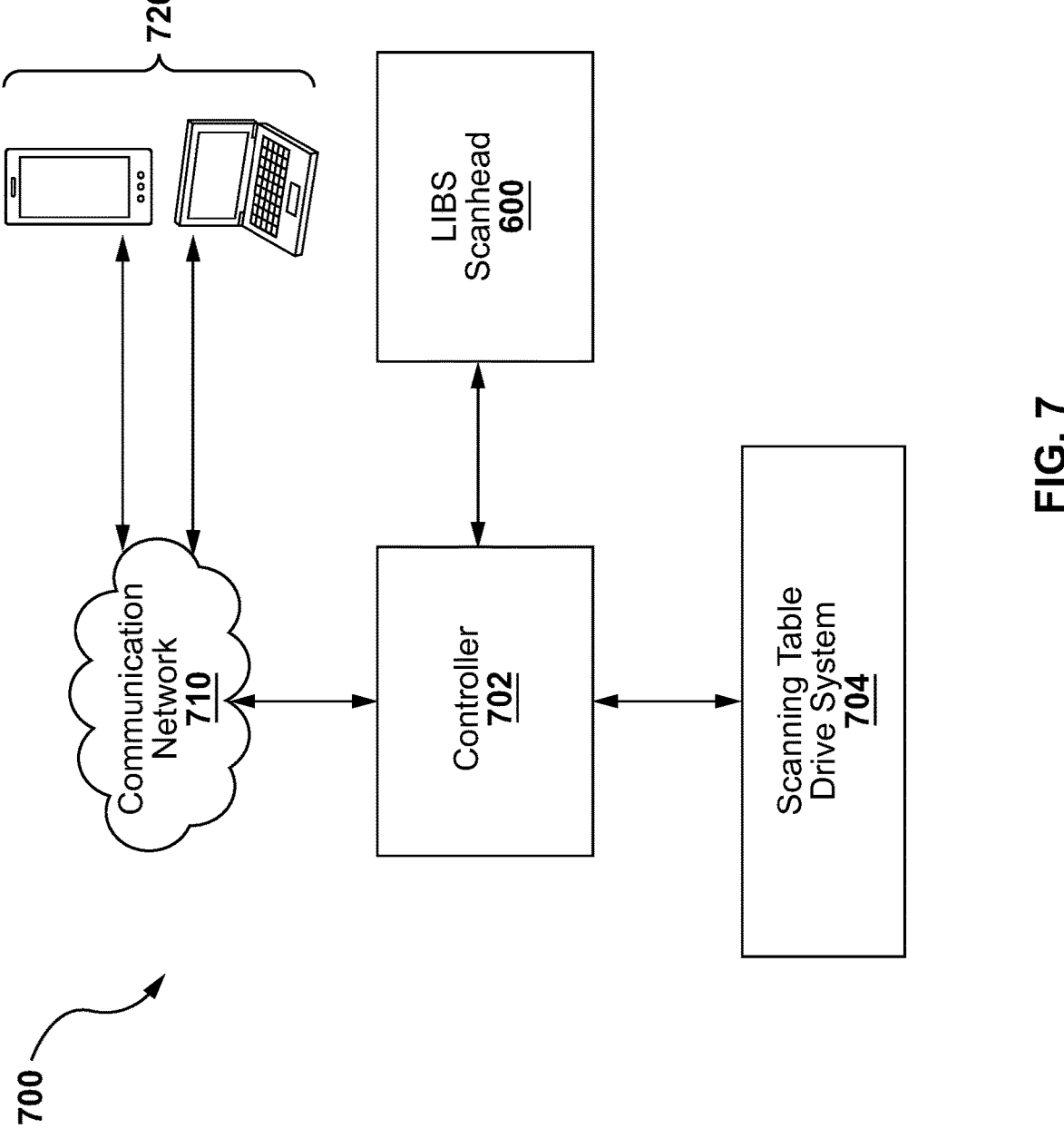
FIG. 7 is a block diagram of a scanning system in accordance with an example embodiment of the present disclosure.
Figure 8:
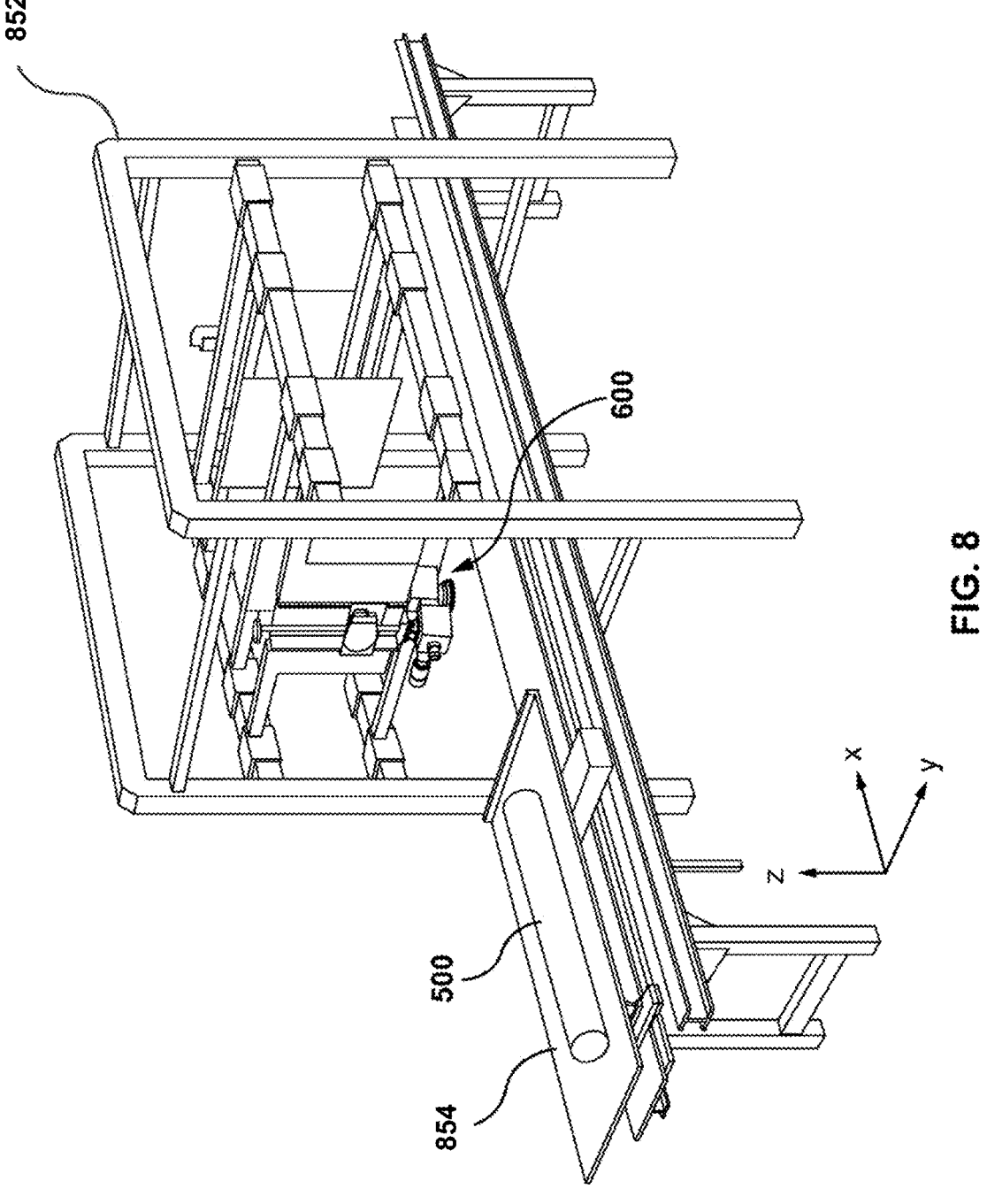
FIG. 8 is a perspective view of the scanning system of FIG. 7 in accordance with an embodiment of the present disclosure.

FIG. 7 is a block diagram of a scanning system 700 in accordance with an example embodiment of the present disclosure. The scanning system 700 comprises a controller 702 coupled to the LIBS scanning head 600, a scanning table drive system 704 for moving the scanning table 854 between table positions, and a plurality of user computing devices 720 (which may be smartphones, tablets, personal computers, or other suitable devices) via a communications network 710 such as the Internet. As shown in FIG. 8, the scanning system 700 may be carried at least in part by a frame 852 to which the moveable scanning table 854 is attached. It will be appreciated that geological cores are elongate, generally cylindrical and relatively heavy and difficult to move by an individual without assistance, tools or equipment. The scanning table drive system 704 is coupled to the moveable scanning table 854, which is elongate and is intended to receive a geological core on an elongate scanning surface thereof so that the length of the geological core extends parallel to the length of the moveable scanning table 854. The scanning table drive system 704 is adapted to the move the scanning table 854 laterally in the direction of the length of the geological core along the axis of the geological core.

The speed at which the scanning table 854 moves during scanning may vary and represents a trade-off between density of sample/test points and the time of acquisition. The scanning speed may vary from, for example, 0.05 mm/s to 50 mm/s. The acquisition area varies based on the first focus lens 610. In one example, the first focus lens 610 provides an acquisition area (scan area) of 40 mm×40 mm. The size of the acquisition area can be changed by changing the first focus lens 610.

Figure 11:
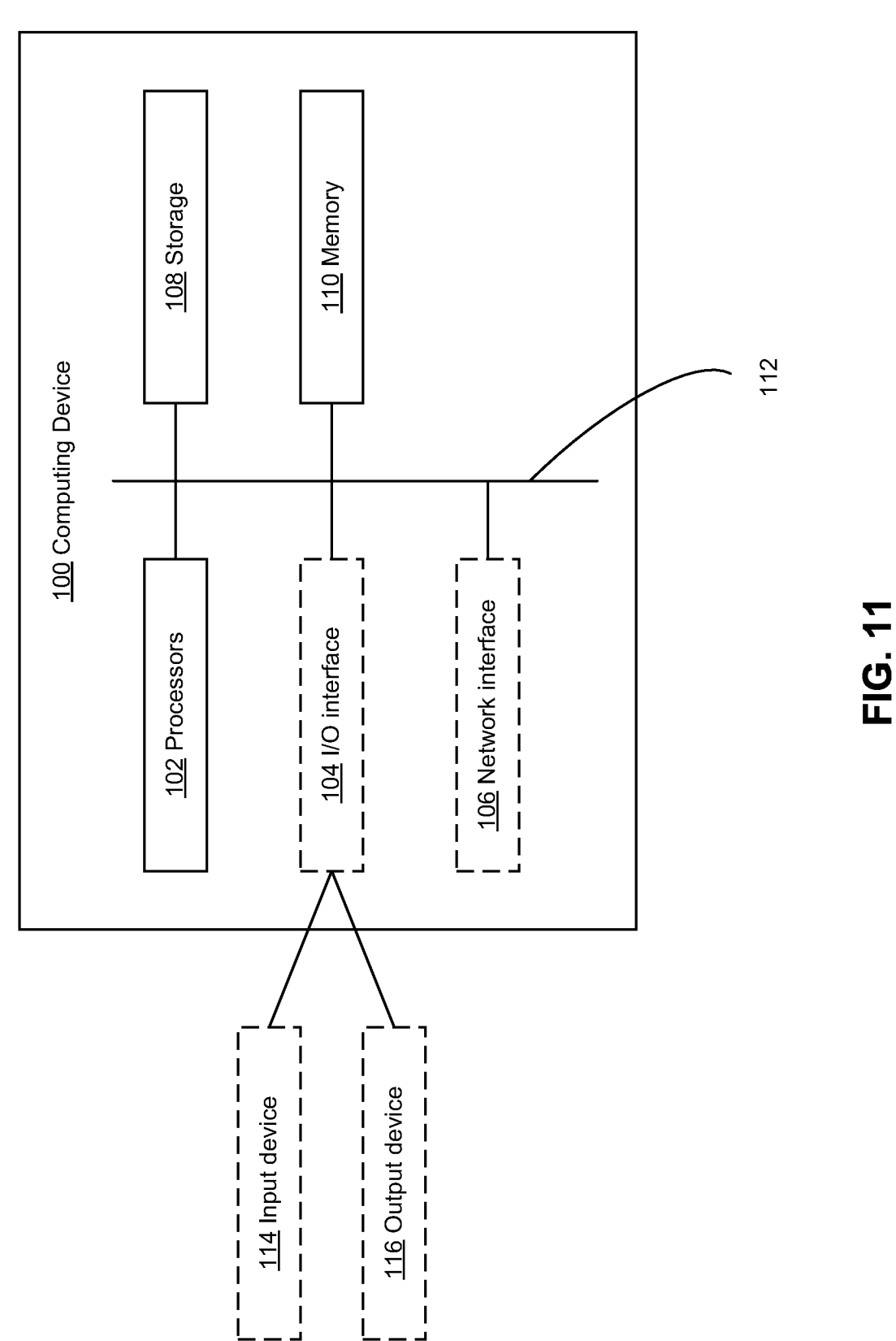
FIG. 11 is a block diagram of an example simplified computing device may be used in accordance with example embodiments of the present disclosure.

FIG. 11 illustrates a block diagram of an example simplified computing device 100, which may be a controller 702 in the scanning system 700 or connect thereto. Other computing devices suitable for implementing embodiments described in the present disclosure may be used, which may include components different from those discussed below. In some examples, the computing device 100 may be implemented across more than one physical hardware unit, such as in a parallel computing, distributed computing, virtual server, or cloud computing configuration. Although FIG. 1 shows a single instance of each component, there may be multiple instances of each component in the computing device 100.

The computing device 100 may include one or more processors which may be a central processing unit (CPU) with a hardware accelerator, a graphics processing unit (GPU), a tensor processing unit (TPU), a neural processing unit (NPU), a microprocessor, an application-specific integrated circuit (ASIC), a field-programmable gate array (FPGA), a dedicated logic circuitry, a dedicated artificial intelligence processor unit, or a combination thereof.

The computing device 100 may also include one or more optional input/output (I/O) interfaces 104, which may enable interfacing with one or more optional input devices 114 and/or optional output devices 116. In the example shown, the input device(s) 114 (e.g., a keyboard, a mouse, a microphone, a touchscreen, and/or a keypad) and output device(s) 116 (e.g., a display, a speaker and/or a printer) are shown as optional and external to the computing device 100. In other examples, one or more of the input device(s) 114 and/or the output device(s) 116 may be included as a component of the computing device 100. In other examples, there may not be any input device(s) 114 and output device(s) 116, in which case the I/O interface(s) 104 may not be needed.

The computing device 100 may include one or more optional network interfaces 106 for wired or wireless communication with a network (e.g., an intranet, the Internet, a P2P network, a WAN and/or a LAN) or other node. The network interfaces 106 may include wired links (e.g., Ethernet cable) and/or wireless links (e.g., one or more antennas) for intra-network and/or inter-network communications.

The computing device 100 may also include one or more storage units 108, which may include a mass storage unit such as a solid state drive, a hard disk drive, a magnetic disk drive and/or an optical disk drive. The computing device 100 may include one or more memories 110, which may include a volatile or non-volatile memory (e.g., a flash memory, a random access memory (RAM), and/or a read-only memory (ROM)). The non-transitory memory 110 may store instructions for execution by the processors 102, such as to carry out examples described in the present disclosure. The memory 110 may include other software instructions, such as for implementing an operating system and other applications/functions. In some examples, memory 110 may include software instructions for execution by the processors 102 to train a neural network and/or to implement a trained neural network, as disclosed herein.

In some other examples, one or more data sets and/or modules may be provided by an external memory (e.g., an external drive in wired or wireless communication with the computing device 100) or may be provided by a transitory or non-transitory computer-readable medium. Examples of non-transitory computer readable media include a RAM, a ROM, an erasable programmable ROM (EPROM), an electrically erasable programmable ROM (EEPROM), a flash memory, a CD-ROM, or other portable memory storage.

There may be a bus 112 providing communication among components of the computing device 100, including the processors 102, optional I/O interface(s) 104, optional network interface(s) 106, storage unit(s) 108 and/or memory(ies) 110. The bus 112 may be any suitable bus architecture including, for example, a memory bus, a peripheral bus or a video bus.

Figure 12:
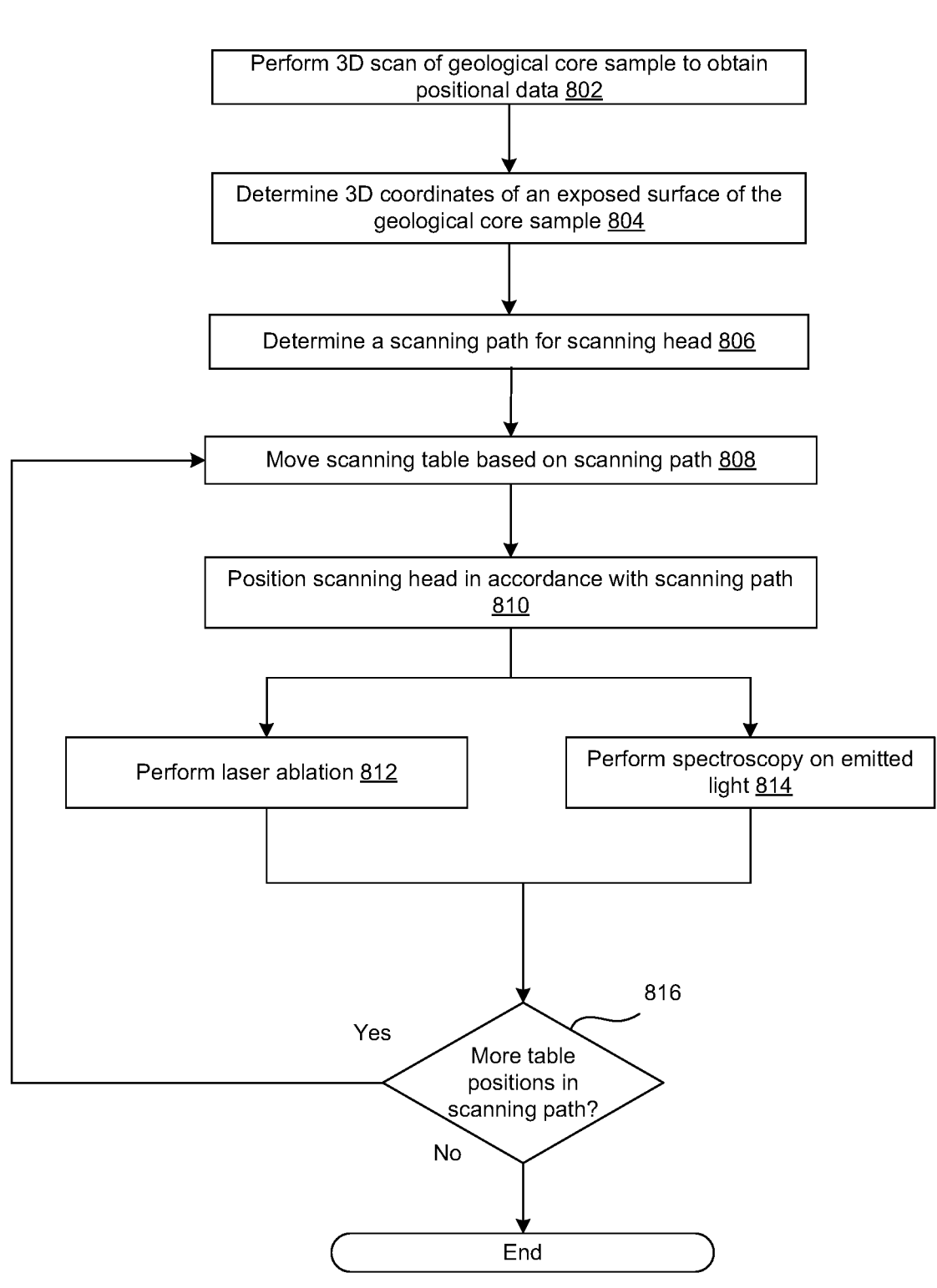
FIG. 12 is a flowchart of a method for laser induced breakdown spectroscopy (LIBS) using a LIBS scanning head in accordance with an example embodiment of the present disclosure.

Referring now to FIG. 12, a flowchart of method 800 for laser induced breakdown spectroscopy using the LIBS scanning head 600 in accordance with one embodiment of the present disclosure will be described. The method 800 is performed at least in part by one or more processors of a computing device 100, namely the controller 704.

At step 802, a three-dimensional (3D) scan of the geological core is performed to generate 3D coordinates of the geological core. The 3D scan is typically performed while the geological core is located on the scanning table 854 of the scanning system 700 and immediately prior to performing a LIBS operation but may be performed in advance. The 3D scan may be performed using a two-dimensional (2D) laser profiler or similar device by performing the scan while moving the scanning table 854. The output of the 2D laser profiler obtained as the scanning table 854 was moved is then combined to generate 3D coordinates of the geological core. Alternatively, the 3D scan may be performed using a LiDAR scanner or other suitable 3D detection and ranging device.

Depending on nature of scanner, coordinates are time-resolved with the position of the scanning table 854 producing 3D coordinates of the geological core surface in table coordinates. Independently of nature of the scanner, the result of this step is 3D coordinates of geological core surface in table frame. The 3D coordinates of the geological core obtained by the scan are then received by the one or more processors 102 of the computing device 100. The 3D coordinates are defined by a 3D point cloud.

At step 804, 3D coordinates of an exposed surface of the geological core relative to a reference are determined by the one or more processors 102 of the computing device 100 based on a 3D coordinates and orientation of the focal plane of the LIBS scanning head 600 relative to the reference, and 3D coordinates of a scanning surface of the scanning table 804 relative to the reference.

At step 806, a scanning path for the LIBS scanning head 600 by determining, for each position in a plurality of positions of the scanning table 854 corresponding to a region of interest of the geological core, a curve of intersection of the focal plane of the LIBS scanning head 600 and the 3D coordinates of the exposed surface of the geological core in the region of interest. The scanning path comprises a plurality of positions of the scanning table 854. In particular, the scanning path extends between a start position and an end position with a plurality of intermediate positions between the start position and end position.

The region of interest may be a 3D or 2D region (e.g., the surface of a cut core) depending on the scale of interest (e.g., the region of interest may appear flat even though it is variable at the microscale or nanoscale). The region of interest may be the whole exposed surface of the geological core or a subset of the exposed surface of the geological core dynamically selected based on sensor data. In some examples, the sensor data for one or more scans of the geological core is obtained via one or more other sensors. The one or more other sensors may comprise one or more hyperspectral cameras, one or more RGB (red, green, blue) cameras, one or more x-ray fluorescence (XRF) spectrometers, a magnetic susceptibility sensor, or other sensors, or a combination thereof. A hyperspectral camera integrates an imaging spectrograph with a monochrome matrix array sensor (camera). An XRF spectrometer is a spectrometer that measures the emission of characteristic "secondary" (or fluorescent) X-rays from a material that has been excited by being bombarded with high-energy X-rays or gamma ray. A magnetic susceptibility sensor measures how much a material will become magnetized in an applied magnetic field. The region of interest is determined based of the geological core based on the sensor data for one or more scans of the geological core obtained via the one or more other sensors. In some examples, determining the region of interest comprises: determining, from the sensor data, one or a combination of a presence of one or more minerals in the geological core, a presence of one or more elements in the geological core, a presence of sulphides in the geological core, alterations in the geological core, or a rock quality of the geological core; and determining the region of interest based of the geological core based on one or a combination of a presence of one or more minerals in the geological core, a presence of one or more elements in the geological core, a presence of sulphides in the geological core, alterations in the geological core, or a rock quality of the geological core.

In at least some examples, the scanning path defines a vertical direction and distance between the LIBS scanning head 600 and the exposed surface of the geological core when located on the scanning surface of the scanning table 854, and a 3D orientation of the focal plane of the LIBS scanning head 600. The orientation of the focal plane of the LIBS scanning head 600 is controlled by the position of the scanning mirror 630. As noted above, the position of the scanning mirror 630 is controlled by galvanometers. By controlling the voltage of a control signal transmitted to the galvanometers, the position of the scanning mirrors 630 is changed by causing the scanning mirrors 630 to rotate in a respective one of the x- and y-axes, collectively allowing the shared optical path to be changed (e.g., rotated) about the two axes. Assuming a proper 3D referencing (or calibration) procedure was applied, galvanometer voltages to position the scanning mirrors 630 appropriately can be calculated to direct the shared optical path (e.g., for the laser and fiber optic receiver) at any point in the field of view (FOV) of the LIBS scanning head 600 given 3D coordinates. Next, 3D coordinates of intersection are transformed into sequence of voltage values for beam directing galvanometers to move the shared optical path (e.g., laser spot) along calculated intersection curve. The calculation can happen either considering moving the scanning table 854 at a certain speed and adjusting the intersection curve according to a moving reference frame or assuming the scanning table 854 remains still for one cycle of acquisition.

Figure 10A:
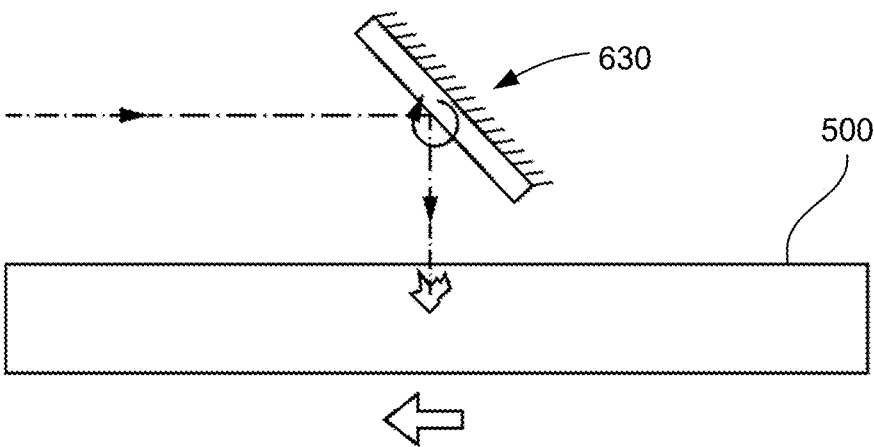
FIGS. 10A and 10B are schematic diagrams showing the focal plane of LIBS scanning head in two different positions.
Figure 10B:
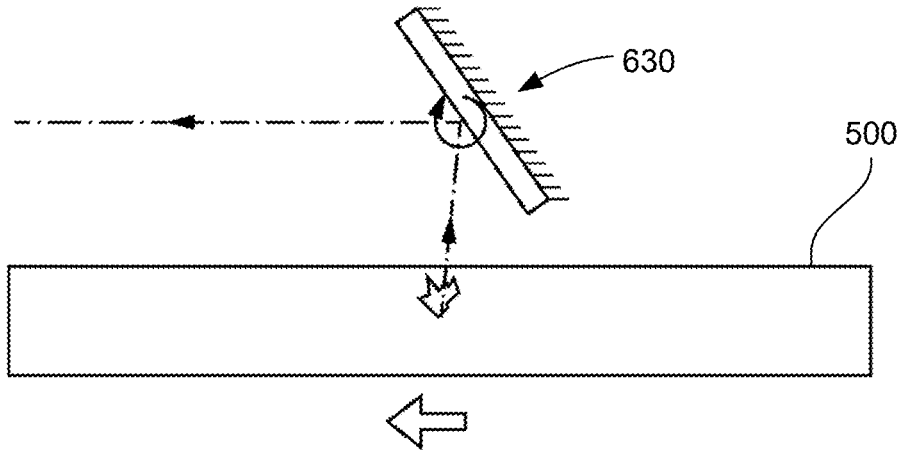

During a scan instance at a table position, the focal plane of the LIBS scanning head 600 is moved across the geologic core sample from one position to another. This is called a scan line or scan cycle and can be seen by a comparison of FIGS. 10A and 10B. As can be seen by comparing FIGS. 10A and 10B, the focal plane of LIBS scanning head 600 is rotate to form a scan line across the geological core. The whole region of interest of the geologic core sample is captured by multiple scan lines/scan cycles at multiple table positions. For each shot on the line/curve of intersection, there is a desired position having a corresponding voltage for a first galvanometer. The corresponding voltage for the second galvanometer is being found in such way that the shared optical path will point to an intersection of a focal plane and exposed surface of the geologic core sample. The intersection will not necessary be straight. Accordingly, the terms "line of intersection" and "curve of intersection" are used interchangeably in the present disclosure. Lens aberration with respect to the first focus lens may adjusted for.

Software either preprograms the controller 704 with voltage sequences for every table position with the scanning table 854 moving at a certain predefined speed (or remaining still) or provides the voltage sequence for the current table position in advance. In the case that the software preprograms the controller 704, the controller 704 may have either algorithmic, electrical or hardware mechanism to resolve table position in real-time. When the table position becomes available for the controller 740, it sequentially applies the provided voltage values to the galvanometers and generates laser pulses to generate plasma. The controller 740 activates one or more spectrometers 640 to capture spectra of produced light. After inducing plasma, the controller 740 may tune the voltage of galvanometer to compensate for movement of scanning table 854, for example, if poor plasma generation occurred (which may be detected automatically by the output of the spectrometers 640 being outside of then normal operating range, and the correction automatically applied). A primary objective is to maintaining quality plasma formation at the focus spot so that the emissions are detected by the spectrometers 640 while moving the scanning table 854. The controller 740 may have an additional electronic device that generates compensations automatically. The compensations may look like a voltage ramp to continuously rotate the scanning mirrors 630 during the spectrometer acquisition phase.

Alternatively, in other embodiments the orientation of the focal plane of the LIBS scanning head 600 could be controlled by rotating the LIBS scanning head 600 itself two-dimensionally. The position of the scanning mirrors 630 within t the LIBS scanning head 600 could remain fixed.

In at least some examples, the scanning path depends on a scanning speed of the scanning head 600 and a speed at which the scanning table 854 moves.

At step 808 the scanning table 854 is moved based on the scanning path by the scanning table drive system 702 based on instructions from the controller 704. Initially, the scanning table 854 is moved to the start position of scanning path.

At step 810, the focal plane of the LIBS scanning head 600 is positioned in accordance with the scanning path based on instructions from the controller 704. Positioning the focal plane of the LIBS scanning head 600 in accordance with the scanning path comprises one or more of: raising or lowering the LIBS scanning head 600 relative to the scanning surface of the scanning table 854 to correspond to the vertical direction and distance defined by the scanning path for the respective position of the scanning table 854; and rotating the shared optical path of the LIBS scanning head 600 so that the position of the focal plane of the LIBS scanning head 600 corresponds to the 3D orientation of the focal plane of the LIBS scanning head 600 defined by the scanning path for the respective position of the scanning table 854.

At step 812, laser ablation forming plasma is performed on the exposed surface of the geological core located on the scanning surface of the scanning table 854 using the oscillating planar focus laser 604 of the LIBS scanning head 600.

At step 814, contemporaneously with performing laser ablation on the exposed surface of the geological core, spectroscopy (e.g., a spectroscopic scan) is performed on the emitted light received by the fiber optic receiver 606 using one or more the spectrometers 640. The spectrometers 640 output spectra readings for each spectroscopic scan which are numbered, indexed, or timestamped. The At step 816, it is determined by the controller 704 whether any more table positions in the scanning path are yet to be scanned. If no table positions in the scanning path are yet to be scanned, the method 800 ends. If one or more table positions in the scanning path are yet to be scanned, the method returns to step 818 at which the scanning table 854 is moved to the next position in the scanning path.

Post-acquisition processing may be performed after the whole region of interest is scanned. The post-acquisition processing may comprise generating a 2D projection of the spectra readings of the geological core based on the numbered, indexed, or timestamped spectra readings output by the one or more the spectrometers 640 during the spectroscopic scan. Generating the 2D projection of the spectra readings may comprise generating a 2D positional (or spatial) map of the geological core from the 3D positional data, correlating the spectra readings of the geological core based on a respective time, index or timestamp at which the respective spectra readings were acquired with a position of the scanning table and the geological core relative to the scanning table 854 at the respective time, index or timestamp, and combining the spectra readings of the geological core using the correlation data. The resultant 2D projection of the spectra readings may be output as a digital image, which may be stored in an appropriate file format in the memory of the controller 704. The 2D projection of the spectra readings of the geological core may be overlayed upon a base digital image of the geological core, such as a hyperspectral image, a natural light (or RGB) photographic image, an XRF image, or other image type. The resultant overlay of the 2D projection of the spectra readings and the base digital image may also be output as a digital image, which may be stored in an appropriate file format in the memory of the controller 704.

The spectra readings, generated images, or other data or information may be output to a display device of the controller 704, for example, within a visual user interface tool of the controller 704 for viewing geological core data. Alternatively, the spectra readings, generated images, or other data or information may be sent to user computing devices 720, for example by sending via the communications network 710, where the spectra readings, generated images, or other data or information may be viewed, stored, etc. a user-based visual user interface tool. It will be appreciated that the scanning system 700 may be operated remotely, for example, at a drilling site and that access to spectra readings, generated images, or other data or information may be desired at other locations, such as an office of a customer or operator of the scanning system 700.

Although the above-noted embodiments describe a LIBS scanning head with a fiber optic receiver, it is contemplated that the fiber optic receiver could be substituted for a suitable photosensitive detector such as a camera (e.g., hyperspectral camera) using a suitable camera adapter in other embodiments. In various embodiments, a photosensitive detector such as a camera can be provided to provide camera imaging in addition to spectrographic analysis, for example, to show exactly where and how plasma samples have been generated for various purposes such as analysis, inspection, and/or quality control. In addition, collected light signals can be split, directed to, and collected by multiple devices such as both a camera and a spectrometer.

General

Through the descriptions of the preceding embodiments, the present disclosure may be implemented by using hardware only, or by using software and a necessary universal hardware platform, or by a combination of hardware and software. The coding of software for carrying out the above-described methods described is within the scope of a person of ordinary skill in the art having regard to the present disclosure. Based on such understandings, the technical solution of the present disclosure may be embodied in the form of a software product. The software product may be stored in a non-volatile or non-transitory storage medium, which can be an optical storage medium, flash drive or hard disk. The software product includes a number of instructions that enable a computing device (personal computer, server, or network device) to execute the methods provided in the embodiments of the present disclosure.

All values and sub-ranges within disclosed ranges are also disclosed. Also, although the systems, devices and processes disclosed and shown herein may comprise a specific plurality of elements, the systems, devices and assemblies may be modified to comprise additional or fewer of such elements. Although several example embodiments are described herein, modifications, adaptations, and other implementations are possible. For example, substitutions, additions, or modifications may be made to the elements illustrated in the drawings, and the example methods described herein may be modified by substituting, reordering, or adding steps to the disclosed methods.

Features from one or more of the above-described embodiments may be selected to create alternate embodiments comprised of a subcombination of features which may not be explicitly described above. In addition, features from one or more of the above-described embodiments may be selected and combined to create alternate embodiments comprised of a combination of features which may not be explicitly described above. Features suitable for such combinations and subcombinations would be readily apparent to persons skilled in the art upon review of the present disclosure as a whole.

In addition, numerous specific details are set forth to provide a thorough understanding of the example embodiments described herein. It will, however, be understood by those of ordinary skill in the art that the example embodiments described herein may be practiced without these specific details. Furthermore, well-known methods, procedures, and elements have not been described in detail so as not to obscure the example embodiments described herein. The subject matter described herein and in the recited claims intends to cover and embrace all suitable changes in technology.

Although the present disclosure and its advantages have been described in detail, it should be understood that various changes, substitutions and alterations can be made herein without departing from the present disclosure as defined by the appended claims.

The present disclosure may be embodied in other specific forms without departing from the subject matter of the claims. The described example embodiments are to be considered in all respects as being only illustrative and not restrictive. The present disclosure intends to cover and embrace all suitable changes in technology. The scope of the present disclosure is, therefore, described by the appended claims rather than by the foregoing description. The scope of the claims should not be limited by the embodiments set forth in the examples, but should be given the broadest interpretation consistent with the description as a whole.

The invention claimed is:

1. A method for laser induced breakdown spectroscopy (LIBS), comprising:
   (i) moving a scanning table with a geological sample disposed upon a scanning surface thereof to a table position in a plurality of table positions defined by a scanning path, wherein the plurality of table positions correspond to a region of interest of the geological sample, the scanning table and the geological sample each being elongate and having a longitudinal axis, the geological sample being disposed on the scanning surface so that a length of the geological sample extends parallel to a length of the scanning table, the scanning table being moved laterally in a direction of the length of the geological sample along the longitudinal axis of the geological sample;
   (ii) positioning a focal plane of a LIBS scanning head in accordance with the table position, the LIBS scanning head comprising an oscillating planar focus laser for performing laser ablation on the geological sample and an optical receiver for receiving light emitted from an ablation site on the geological sample, the oscillating planar focus laser and the optical receiver having a shared optical path with a focus lens of the LIBS scanning head at one end, the LIBS scanning head being adapted to two-dimensionally rotate the shared optical path to control a position of the focal plane of the LIBS scanning head, the LIBS scanning head being mounted to be moveable relative to the scanning surface of the scanning table, wherein the focal plane forms an intersection with a surface of the geological sample, the intersection comprising multiple focused points on the surface;
   (iii) performing laser ablation on the geological sample using the oscillating planar focus laser of the LIBS scanning head; and
   (iv) contemporaneously with performing the laser ablation on the geological sample, performing spectroscopy on the geological sample, performing spectroscopy on the emitted light received by the optical receiver; wherein steps (i) to (iv) are performed for each table position in the plurality of table positions.

2. The method of claim 1, wherein the method is performed sequentially from a start position of the plurality of table positions to an end position of the plurality of table positions.

3. The method of claim 1, further comprising:
   receiving three-dimensional (3D) coordinates of the geological sample;
   determining 3D coordinates of an exposed surface of the geological sample relative to a reference based on a 3D coordinates and orientation of the focal plane of the LIBS scanning head relative to the reference, and 3D coordinates of the scanning surface of the scanning table relative to the reference; and
   determining the scanning path by determining, for each position in the plurality of table positions of the scanning table corresponding to the region of interest of the geological sample, a curve of intersection of the focal plane of the LIBS scanning head and the 3D coordinates of the exposed surface of the geological sample in the region of interest.

4. The method of claim 1, wherein the scanning path defines a vertical direction and distance between the LIBS scanning head and the exposed surface of the geological sample when located on the scanning surface of the scanning table, and a 3D orientation of the focal plane of the LIBS scanning head.

5. The method of claim 4, wherein positioning the focal plane of the LIBS scanning head in accordance with the table position comprises one or more of:
   moving the LIBS scanning head relative to the scanning surface of the scanning table to correspond to the vertical direction and distance defined by the scanning path for the respective position of the table position; and
   rotating the shared optical path of the LIBS scanning head so that the position of the focal plane of the LIBS scanning head corresponds to the 3D orientation of the focal plane of the LIBS scanning head defined by the scanning path for the respective table position.

6. The method of claim 1, further comprising:
   obtaining sensor data for one or more scans of the geological sample obtained via one or more other sensors;
   determining the region of interest based of the geological sample based on the sensor data for one or more scans of the geological sample obtained via the one or more other sensors.

7. The method of claim 6, wherein determining the region of interest comprises:
   determining, from the sensor data, one or a combination of a presence of one or more minerals in the geological sample, a presence of one or more elements in the geological sample, a presence of sulphides in the geological sample, alterations in the geological sample, or a rock quality of the geological sample; and
   determining the region of interest based of the geological sample based on one or a combination of the presence of one or more minerals in the geological sample, the presence of one or more elements in the geological sample, the presence of sulphides in the geological sample, the alterations in the geological sample, or the rock quality of the geological sample.

8. The method of claim 6, wherein the one or more other sensors comprise one or more hyperspectral cameras, one or more RGB (red, green, blue) cameras, one or more x-ray fluorescence (XRF) spectrometers, a magnetic susceptibility sensor, or a combination thereof.

9. The method of claim 1, wherein the region of interest is a dynamically selected region of interest.

10. The method of claim 1, wherein the region of interest is a whole exposed surface of the geological sample.

11. The method of claim 1, wherein the scanning path depends on a scanning speed of the scanning head and a speed at which the scanning table moves.

12. The method of claim 1, further comprising:

generating a two-dimensional (2D) projection of spectra readings of the geological sample generated by the spectroscopy; and overlaying the 2D projection of the spectra readings upon a base digital image of the geological sample.

13. The method of claim 12, wherein the base digital image is a hyperspectral image, a natural light (or RGB) photographic image, or an XRF image.

14. The method of claim 1, wherein performing spectroscopy comprises performing one or a combination of visible light spectroscopy, ultraviolet light spectroscopy or infrared light spectroscopy.

15. A laser induced breakdown spectroscopy (LIBS) scanning system, comprising:

a LIBS scanning head comprising:

a housing;

an oscillating planar focus laser received in the housing, the oscillating planar focus laser having a laser light emission path along which laser light is directed;

an optical receiver received in the housing, the optical receiver having an optical output port, the optical receiver having a light reception path along which observed natural light is received, wherein the light reception path is perpendicular to the laser light emission path;

a dichroic element received in the housing and oriented at 45 degrees relative to the light reception path and the laser light emission path;

a first focus lens received in the housing for focusing the laser light emitted by the oscillating planar focus laser and receiving natural light; and a pair of rotatable scanning mirrors received in the housing and located between the dichroic element and the first focus lens, the dichroic element and the pair of scanning mirrors being arranged to provide a shared optical path for the laser light emitted by the oscillating planar focus laser and natural light between the dichroic element and the first focus lens, the pair of scanning mirrors being adapted to two-dimensionally rotate the shared optical path to define a position of a focal plane of the LIBS scanning head, wherein the dichroic element is positioned for directing light emitted by the oscillating planar focus laser along the shared optical path and directing the natural light for reception by the optical receiver, wherein the focal plane forms an intersection with a surface of the geological sample, the intersection comprising multiple focused points on the surface; and and one or more spectrometers coupled to the optical receiver, the one or more spectrometers selected from the group consisting of a visible light spectrometer, ultraviolet light spectrometer, and infrared light spectrometer.

16. A scanning system for geological samples, comprising:

a scanning table having a scanning surface;

a laser induced breakdown spectroscopy (LIBS) scanning head mounted to be moveable relative to the scanning surface of the scanning table, the LIBS scanning head comprising:

a housing;

an oscillating planar focus laser received in the housing, the oscillating planar focus laser having a laser light emission path along which laser light is emitted;

an optical receiver received in the housing, the optical receiver having a optical output port, the optical receiver having a light reception path along which observed natural light is received, wherein the light reception path is perpendicular to the laser light emission path;

a dichroic element received in the housing and oriented at 45 degrees relative to the light reception path is perpendicular to the laser light emission path;

a first focus lens received in the housing for focusing the laser light emitted by the oscillating planar focus laser and receiving natural light; and a pair of rotatable scanning mirrors received in the housing and located between the dichroic element and the first focus lens, the dichroic element and the pair of scanning mirrors being arranged to provide a shared optical path for the laser light emitted by the oscillating planar focus laser and natural light between the dichroic element and the first focus lens, the pair of scanning mirrors being adapted to two-dimensionally rotate the shared optical path to define a focal plane of the LIBS scanning head, wherein the dichroic element is positioned for directing light emitted by the oscillating planar focus laser along the shared optical path and directing the natural light for reception by the optical receiver, wherein the focal plane forms an intersection with a surface of the geological sample, the intersection comprising multiple focused points on the surface;

a controller for controlling the moveable scanning table and controlling the LIBS scanning head, wherein the controller is configured to:

(i) cause the scanning table to move with the geological sample disposed upon the scanning surface thereof to a table position in a plurality of table positions defined by a scanning path, wherein the plurality of table positions correspond to a region of interest of the geological sample, the scanning table and the geological sample each being elongate and having a longitudinal axis, the geological sample being disposed on the scanning surface so that a length of the geological sample extends parallel to a length of the scanning table, the scanning table being moved laterally in a direction of the length of the geological sample along the longitudinal axis of the geological sample;

(ii) cause the focal plane of the LIBS scanning head to be positioned in accordance with the table position;

(iii) cause laser ablation to be performed on the geological sample using the oscillating planar focus laser of the LIBS scanning head; and (iv) contemporaneously with performing laser ablation on the geological sample, cause spectroscopy to be performed on the emitted light received by the optical receiver;

wherein steps (i) to (iv) are performed for each table position in the plurality of table positions.

17. The scanning system of claim 16, further comprising:
a second focus lens received in the housing and located between the dichroic element and the optical receiver, the second focus lens focuses received natural light prior to reception by the optical receiver.

18. The scanning system of claim 16, wherein the optical receiver is a fiber optic receiver.

19. The scanning system of claim 16, wherein the controller is configured to:
receive three-dimensional (3D) coordinates of the geological sample;
determine 3D coordinates of an exposed surface of the geological sample relative to a reference based on a 3D coordinates and orientation of the focal plane of the LIBS scanning head relative to the reference, and 3D coordinates of the scanning surface of the scanning table relative to the reference, the LIBS scanning head comprising an oscillating planar focus laser for performing laser ablation on the geological sample and the optical receiver for receiving light emitted from an ablation site on the geological sample, the oscillating planar focus laser and the optical receiver having a shared optical path with a focus lens of the LIBS scanning head at one end, the LIBS scanning head being adapted to two-dimensionally rotate the shared optical path to control a position of the focal plane of the LIBS scanning head, the LIBS scanning head being mounted to be moveable relative to the scanning surface of the scanning table;
determine a scanning path for the LIBS scanning head by determining, for each position in the plurality of table positions of the scanning table corresponding to a region of interest of the geological sample, a curve of intersection of the focal plane of the LIBS scanning head and the 3D coordinates of the exposed surface of the geological sample in the region of interest;
cause the scanning table to move from a start position to an end position for each position in the plurality of table positions of the scanning table corresponding to the region of interest of the geological sample;
during the movement of the scanning table from the start position to the end position, at each position in the plurality of table positions of the scanning table corresponding to the region of interest of the geological sample:
cause the focal plane of the LIBS scanning head to be positioned in accordance with the scanning path;
cause laser ablation to be performed on the exposed surface of the geological sample located on the scanning surface of the scanning table using the oscillating planar focus laser of the LIBS scanning head; and
contemporaneously with performing laser ablation on the exposed surface of the geological sample, cause spectroscopy to be performed on the emitted light received by the the optical receiver.

20. The scanning system of claim 16, wherein the first focus lens is an F-Theta lens.

21. A method for laser induced breakdown spectroscopy (LIBS), comprising:
receiving three-dimensional (3D) coordinates of the geological sample;
determining 3D coordinates of an exposed surface of the geological sample relative to a reference based on a 3D coordinates and orientation of the focal plane of a LIBS scanning head relative to the reference, and 3D coordinates of a scanning surface of a scanning table relative to the reference;
determining a scanning path for the LIBS scanning head by determining, for each position in a plurality of table positions of the scanning table corresponding to a region of interest of the geological sample, a curve of intersection of the focal plane of the LIBS scanning head and the 3D coordinates of the exposed surface of the geological sample in the region of interest;
moving the scanning table from a start position to an end position for each position in the plurality of table positions of the scanning table corresponding to the region of interest of the geological sample;
during the movement of the scanning table from the start position to the end position, at each position in the plurality of table positions of the scanning table corresponding to the region of interest of the geological sample:
positioning the focal plane of the LIBS scanning head in accordance with the scanning path;
performing laser ablation on the exposed surface of the geological sample located on the scanning surface of the scanning table using an oscillating planar focus laser of the LIBS scanning head; and
contemporaneously with performing laser ablation on the exposed surface of the geological sample, performing spectroscopy on the emitted light received by an optical receiver.

22. The method of claim 21, the scanning table and the geological sample each being elongate and having a longitudinal axis, the geological sample being disposed on the scanning surface so that a length of the geological sample extends parallel to a length of the scanning table, the scanning table being moved laterally in a direction of the length of the geological sample along the longitudinal axis of the geological sample.

23. The method of claim 1, wherein the optical receiver is a fiber optic receiver.

24. The scanning system of claim 15, wherein the optical receiver is a fiber optic receiver.

25. The scanning system of claim 24, further comprising a fiber optic splitter or multi- furcated fiber, the fiber optic splitter or multi-furcated fiber coupled to the fiber optic receiver and having a plurality of fiber optic output ports,
wherein the one or more spectrometers comprise a plurality of spectrometers coupled to the fiber optic output ports of the fiber optic splitter or multi-furcated fiber, the plurality of spectrometers selected from the group consisting of a visible light spectrometer, ultraviolet light spectrometer, and infrared light spectrometer.

26. The scanning system of claim 18, further comprising:
a fiber optic splitter coupled to the fiber optic receiver, the fiber optic splitter having a plurality of fiber optic output ports; or
multi-furcated fiber coupled to the fiber optic receiver, the multi-furcated fiber having a plurality of fiber optic output ports;
a plurality of spectrometers coupled to the fiber optic output ports of the fiber optic splitter or multi-furcated fiber, the spectrometers selected from the group consisting of a visible light spectrometer, ultraviolet light spectrometer, and infrared light spectrometer;
wherein the spectrometers are coupled to the controller, wherein the spectrometers output spectral data to the controller, wherein the controller is configured to store the spectral data received from the spectrometers.

27. The method of claim 1, wherein the LIBS scanning head is mounted to the scanning table to be vertically moveable relative to the scanning surface of the scanning table.

28. The system of claim 15, wherein the LIBS scanning head is mounted to the scanning table to be vertically moveable relative to the scanning surface of the scanning table.

29. The system of claim 16, wherein the LIBS scanning head is mounted to the scanning table to be vertically moveable relative to the scanning surface of the scanning table.

30. The method of claim 1, wherein the geological sample comprises a geological core.

31. The system of claim 15, wherein the geological sample comprises a geological core.

32. The system of claim 16, wherein the geological sample comprises a geological core.

* * * * *